United States Patent [19]

Halvorson

[11] Patent Number: 4,847,764
[45] Date of Patent: Jul. 11, 1989

[54] SYSTEM FOR DISPENSING DRUGS IN HEALTH CARE INSTITUTIONS

[75] Inventor: Jerry L. Halvorson, Rapid City, S. Dak.

[73] Assignee: Meditrol, Inc., Rapid City, S. Dak.

[21] Appl. No.: 53,067

[22] Filed: May 21, 1987

[51] Int. Cl.⁴ .............................................. G06F 15/42
[52] U.S. Cl. ............................. 364/413.02; 364/479; 221/2; 340/309.4
[58] Field of Search ..................... 221/2, 3; 340/309.4; 364/413, 415, 479, 413.02

[56] References Cited

U.S. PATENT DOCUMENTS

| | | |
|---|---|---|
| 3,599,152 | 8/1971 | Williams . |
| 3,606,959 | 12/1968 | Stonor ....................................... 221/2 |
| 3,917,045 | 11/1975 | Williams et al. . |
| 3,998,356 | 12/1976 | Christensen ............................... 221/2 |
| 4,293,845 | 10/1981 | Villa-Real ....................... 340/309.15 |
| 4,473,884 | 9/1984 | Behl ..................................... 221/3 X |
| 4,695,954 | 9/1987 | Rose ..................................... 221/3 X |
| 4,725,997 | 2/1988 | Urquhart .................................. 221/2 |
| 4,733,362 | 3/1988 | Haraguchi ........................... 221/2 X |

FOREIGN PATENT DOCUMENTS 936501 11/1973 Canada .

Primary Examiner—Jerry Smith
Assistant Examiner—Steven G. Kibby
Attorney, Agent, or Firm—Merchant, Gould, Smith, Edell, Welter & Schmidt

[57] ABSTRACT

A system for dispensing medications in a health care institution includes a computer system connected to control a plurality of remote medication dispensers. Pharmacy terminals are provided for entering medication orders and software in the computer system controls the dispensers to dispense medications according to the orders specified. The system includes support for dispensing medications from floor stocks. In either case, medications are administered in accordance with instructions from the computer system generated in accordance with said orders. The system further includes software for identifying medication duplications and potentially dangerous drug interactions based on orders entered into the system at the pharmacy. Inventory control and restocking features are also provided.

97 Claims, 12 Drawing Sheets

© 1988 Meditrol, Inc. (17 U.S.C. 401)

| SCHEDULER 95 |
|---|
| REFERENCE NAME OF EVENT |
| The time specifiers used to cause execution of the program |
| MOH — Minute of Hour |
| HOD — Hour of Day |
| DOW — Day of Week |
| DOM — Day of Month |
| MOY — Month of Year |
| PROGRAM NAME WITH EXECUTION ARGUMENTS |

© 1988 Meditrol, Inc. (17 U.S.C. 401)

FIG. 4

| DATABASE FILES | |
|---|---|
| INSTITUTION MASTER | DRUG BRAND |
| ROOM BED | DRUG THERAPEUTIC EQUIVALENT |
| STATION MASTER | DRUG ORDER |
| STATION DRUG | INVENTORY SITES |
| STATION SLEEVE | DRUG INVENTORY QUANTITY |
| SLEEVE SIZE | CANNED MASTER |
| DISPENSER ROUTES | PATIENT MASTER |
| FORM DICTIONARY | PATIENT ORDERS |
| FREQUENCY CODES | PATIENT HISTORY |
| ROUTE DICTIONARY | MEDICATION HISTORY |
| ALLERGY DICTIONARY | PERSONNEL MASTER |
| DRUG MASTER | PERSONNEL PATIENTS |
| DRUG GENERIC | SCHEDULER |

FIG. 5

| INSTITUTION MASTER 70 |
|---|
| INSTITUTION REFERENCE CODE |
| DESCRIPTION FIELD USED PRIMARILY FOR REPORT TITLES |

FIG. 6

| ROOM BED 71 |
|---|
| ROOM-BED DEFINITION CODE |
| INSTITUTION REFERENCE CODE FOR THE BED |
| THE STATION REFERENCE CODE FOR THE BED |
| IDENTIFICATION OF THE PATIENT CURRENTLY OCCUPYING THE BED |

© 1988 Meditrol, Inc. (17 U.S.C. 401)

FIG. 7

| |
|---|
| STATION MASTER 72 |
| INSTITUTION REFERENCE CODE FOR THIS STATION |
| STATION REFERENCE NAME |
| STATION TYPE INDICATOR (nursing, pharmacy, inquiry, system, etc.) |
| OPERATIONAL STATUS INDICATOR (online, offline, training) |
| DISPENSING METHOD AT NURSING STATIONS (indicates whether the station is employing mechanical dispensers, a cart exchange, or a floor stock system) |
| COMPUTER CONSOLE PORT IDENTIFICATION |
| TERMINAL TYPE INDICATOR (CRT, Printer, or combinations) |
| PRINTER CONNECTION INDICATOR (none, CRT auxillary port, direct connect to the computer, or dispenser mupltiplexer port) |
| PRINTER MODEL INDICATOR |
| NUMBER OF LINES TO SPACE UP THE PAPER UPON COMPLETION OF PRINTING |
| TIMEOUT FACTOR Used to Return the Terminal to an Idle State if it is Left Unattended |
| HELLO CHARACTER Used to Certify the Transmissions with each Dispenser |
| DISPENSING STATION NUMBER |
| FIRST DOSE INVENTORY SITE IDENTIFICATION |
| RESTOCK INVENTORY SITE IDENTIFICATION |

© 1988 Meditrol, Inc. (17 U.S.C. 401)

FIG. 8

| STATION MASTER 73 |
|---|
| IDENTIFICATION OF THE DRUG |
| NUMBER OF PATIENTS BEING SERVICED BY THIS STATION THAT REQUIRE THIS DRUG ON A ROUTINE (RTN) SCHEDULE |
| NUMBER OF DOSES NEEDED FOR THE RTN MEDICATIONS AT THIS STATION |
| NUMBER OF PATIENTS BEING SERVICED BY THIS STATION THAT REQUIRE THIS DRUG ON AN AS NEEDED (PRN) BASIS |
| NUMBER OF DOSES NEEDED FOR THE PRN MEDICATIONS AT THIS STATION |
| CURRENT QUANTITY OF THE DRUG AT THE STATION |
| MINIMUM QUANTITY TO MAINTAIN AT THE STATION |
| DATE AND TIME OF LAST USAGE |
| RETENTION FACTOR WHICH IS ONE OF THE PARAMETERS USED IN THE EQUATION TO COMPUTE THE UNUSED ELAPSED TIME NECESSARY BEFORE THE REMAINING QUANTITY OF THE DRUG IS RETURNED TO THE PHARMACY INVENTORY STOCK |

FIG. 9

| STATION SLEEVE 74 |
|---|
| IDENTIFICATION OF THE DRUG CURRENTLY IN THE SLEEVE, IF ANY |
| CURRENT QUANTITY OF DOSES OF THE DRUG IN THE SLEEVE |
| QUANTITY OF DOSES IN THE SLEEVE WHEN INSTALLED |
| DATE AND TIME WHEN THE SLEEVE WAS INSTALLED |
| QUANTITY OF DOSES IN THE SLEEVE AT THE LAST CABINET REFILL |
| SLOT PARAMETERS CONTAIN INFORMATION SUCH AS SLOT HEIGHT AND HORIZONTAL SPACE LIMITATIONS THAT MUST BE CONSISDERED WHEN INSTALLING A NEW DRUG IN THE DISPENSER |
| CURRENT SLEEVE TYPE IN THIS SLOT |

FIG. 10

| SLEEVE SIZE 75 |
|---|
| SLEEVE IDENTITFIER CODE |
| SLEEVE COLOR (the sleeves may be color coded to coincide with the sleeves capacity) |
| SLEEVE CAPACITY (the number of doses the sleeve is capable of holding) |

© 1988 Meditrol, Inc. (17 U.S.C. 401)

FIG. 11

| DISPENSER ROUTES 76 |
|---|
| ROUTE NUMBER |
| ROUTE TITLE |
| IN-SERVICE INDICATOR |
| ARRAY DEFINING THE HOURS OF THE WEEK FOR SCHEDULED RELOADING OF THE DISPENSERS ON THIS ROUTE |
| ARRAY IDENTITYING THE STATIONS ON THE ROUTE |

FIG. 12

| FORM DICTIONARY 77 |
|---|
| FORM CODE |
| (tablet, capsule, injection, etc.) |

FIG. 13

| FREQUENCY CODES 78 |
|---|
| INSTITUTION REFERENCE CODE |
| FREQUENCY CODE |
| (QID, TID, BID, AM, etc.) |
| SCHEDULED HOURS FOR ADMINISTRATION |

FIG. 14

| ROUTE DICTIONARY 79 |
|---|
| ROUTE OF ADMINISTRATION |
| (oral, topical, rectal, etc.) |

FIG. 15

| ALLERGY DICTIONARY 80 |
|---|
| GROUP IDENTIFICATION CODE |
| DESCRIPTION OF ALLERGY |

© 1988 Meditrol, Inc. (17 U.S.C. 401)

FIG. 16

| DRUG MASTER 81 |
|---|
| GENERIC NAME |
| CURRENTLY USED BRAND (trade) NAME |
| STRENGTH OF THE PACKAGE |
| FORM OF MEDICATION |
| PERFERRED ROUTE OF ADMINISTRATION |
| SLEEVE DEFINITION PARAMETERS (dimensions of package & preferred sleeve) |
| MAXIMUM NUMBER OF DAYS THAT AN ORDER MAY BE WRITTEN FOR |
| NATIONAL DRUG CODE (NDC number) |
| CONTROLLED SUBSTANCE CLASSIFICATION CODE |
| THRERAPEUTIC CLASSIFICATION CODE |
| FORMULARY INDICATOR |
| DISPENSE LOCATION (Dispenserable, Pharmacy delivery, Floor stock, etc.) |
| ISSUE PACKAGE TYPE (Unit dose, Multi-dose, Bulk) |
| STANDARDIZED ADMINISTRATION INFORMATION AND WARNINGS |
| PRICING INFORMATION |
| INVENTORY QUANTITY |

FIG. 17

| DRUG GENERIC 82 |
|---|
| GENERIC DRUG NAME |
| THERAPEUTIC EQUIVALENCE CODE FOR THIS DRUG |
| DRUG-DRUG INTERACTION CODE FOR THIS DRUG |
| ARRAY OF DRUG-DRUG INTERACTION CODES THAT INTERACT WITH THIS DRUG |

FIG. 18

| DRUG BRAND 83 |
|---|
| BRAND (trade) NAME |
| CORRESPONDING GENERIC NAME |

FIG. 19

| DRUG THREAPEUTIC EQUIVALENT 84 |
|---|
| THREAPEUTIC CODE |
| DESCRIPTION OF THE CLASSIFICATION |

© 1988 Meditrol, Inc. (17 U.S.C. 401)

FIG. 20

| DRUG ORDER 85 |
|---|
| DRUG IDENTIFICATION |
| RE-ORDER POINT IN ISSUE UNITS |
| NUMBER OF ISSUE UNITS PER ORDER UNIT |
| ORDER UNIT'S DEFINITION |
| DEFAULT ORDER QUANTITY IN ORDER UNITS |
| PRIMARY SUPPLIER IDENTIFICATION |
| PRIMARY SUPPLIER'S DRUG ORDER CODE |
| SECONDARY SUPPLIER'S IDENTIFICATION |
| SECONDARY SUPPLIER'S DRUG ORDER CODE |
| DATE THE LAST ORDER WAS PLACED |
| REFERENCE NUMBER OF THE LAST ORDER |
| DATE THE LAST ORDER WAS RECEIVED |
| QUANTITY RECEIVED IN THE LAST ORDER |
| QUANTITY ON ORDER IN ISSUE UNITS |

FIG. 21

| INVENTORY SITES 86 |
|---|
| SITE IDENTIFICATION NUMBER |
| SITE NAME |
| STANDARD HOURS OF OPERATION OF EACH DAY OF THE WEEK |
| HOLIDAY HOURS OF OPERATION |
| STATION NAME WHERE RESTOCK NOTICES ARE PRINTED |
| STATION NAME WHERE REPORTS ARE PRINTED |
| ALTERNATE SITE TO REFER TO WHEN THIS SITE IS NOT IN OPERATION |
| NUMBER OF THE SITE THAT RESTOCKS THIS SITE |

FIG. 22

| DRUG INVENTORY QUANTITY 87 |
|---|
| INVENTORY SITE NUMBER |
| CURRENT QUANTITY AT THE SITE |
| REORDER POINT (The minimum quantity allowed without restocking) |

© 1988 Meditrol, Inc. (17 U.S.C. 401)

FIG. 23

| CANNED MASTER 88 |
|---|
| DOCTOR IDENTIFICATION |
| DRUG IDENTIFICATION |
| CANNED ORDER NUMBER |
| DRUG DOSAGE |
| ORDER TYPE (PRN, RTN, etc.) |
| FREQUENCY CODE |
| NUMBER OF DAYS TO RUN |
| HOLD STATUS |

FIG. 24

| PATIENT MASTER 89 |
|---|
| IDENTIFICATION NUMBER (ID) |
| NAME |
| DATE OF BIRTH |
| PERSONAL DATA (height, weight, sex, etc.) |
| ADMITTING DATE AND TIME |
| ATTENDING PHYSICIAN |
| PRIMARY NURSE |
| LOCATION (institution, ward, room, bed) |
| DATE AND TIME OF LAST BED ASSIGNMENT |
| DISCHARGE CODE (Released, Deceased, Transferred, etc.) |
| DESCRIPTION OF DIAGNOSIS |
| DESCRIPTION OF ALLERGIES |
| GLOBAL HOLD INDICATORS (holds for all orders for this patient) |

© 1988 Meditrol, Inc. (17 U.S.C. 401)

FIG. 25

| PATIENT ORDER 90 ||
|---|---|
| PATIENT IDENTIFICATION | DRUG NAME (generic and brand) |
| DRUG FORM | ROUTE OF ADMINISTRATION |
| ACTUAL DOSAGE | FREQUENCY CODE |
| QUANTITY OF PACKAGES TO ISSUE PER MEDICATION | DATE AND TIME OF FIRST DOSE |
| DATE AND TIME OF LAST RENEWAL | DATE AND TIME THE LAST DOSE WAS RECEIVED |
| NUMBER OF DOSES RECEIVED | DATE AND TIME LAST DOSE WAS ISSUED |
| NUMBER OF PACKAGES ISSUED | HOLD INDICATORS (NPO, Surgery, General, etc.) |
| HOLD START AND STOP DATE AND TIME | DISCONTINUED INDICATOR |
| ISSUING PACKAGE TYPE (Unit dose, Multi-dose, Bulk) | TYPE OF MEDICATION REGIME (Routine, PRN, etc.) |
| RECEIVE FROM LOCATION (Dispenser, Cart, Floor stock, etc.) | ARRAY OF 24 ELEMENTS USED TO INDICATE THE SCHEDULED HOURS OF ADMINISTRATION |
| INTERVAL INDICATOR (Every day, Even days, Odd days, Specific days, etc.) | ESTIMATED USAGE PER DAY |
| ^ | MINIMUM HOURS BETWEEN DOSES |
| MAXIMUM HOURS BETWEEN DOSES | MAXIMUM DAYS TO ADMINSTER LIMIT |
| MAXIMUM DOSE TO ADMINISTER LIMIT | STAT INDICATOR |
| ADMINISTRATION INFORMATION AND WARNINGS | THERAPEUTIC EQUIVALENT CODE |
| IDENTIFICATION OF ORDERING PHYSICIAN | IDENTIFICATION OF ENTRY AND MODIFICATION PERSONNEL |
| PRICE OF THE MEDICATION | DRUG-DRUG INTERACTION CODE |

FIG. 26

| PATIENT HISTORY 91 |
|---|
| THE DATE AND TIME OF THE TRANSACTION |
| TRANSACTION RECORD TYPE (drug charge, drug credit, bed change, etc.) |
| IDENTIFICATION OF THE PERSONNEL ASSOCIATED WITH THIS TRANSACTION |
| DRUG IDENTIFICATION |
| QUANTITY OF DRUG |
| PRICE OF MEDICATION |
| PATIENT IDENTIFICATION |
| PATIENT LOCATION |

© 1988 Meditrol, Inc. (17 U.S.C. 401)

FIG. 27

| MEDICATION HISTORY 92 |
|---|
| THE DATE AND TIME OF THE TRANSACTION |
| TRANSACTION RECORD TYPE (drug charge or drug credit) |
| IDENTIFICATION OF THE PERSONNEL ASSOCIATED WITH THIS TRANSACTION |
| DRUG IDENTIFICATION |
| QUANTITY OF DRUG |
| DISPENSING LOCATION (Dispenser, Pharmacy, etc.) |
| PRICE OF MEDICATION |
| PATIENT IDENTIFICATION |
| PATIENT LOCATION |

FIG. 28

| PERSONNEL MASTER 93 |
|---|
| IDENTIFICATION NUMBER (system assigned) |
| FULL NAME |
| DEPARTMENT CODE (Pharmacy, Nursing, etc.) |
| ACTIVE INDICATOR |
| PASSWORD |
| INSTITUTION THAT EMPLOYEE IS WORKING IN |
| EMPLOYEE TITLE (Head, Supervisor, Staff, etc.) |
| WORK AREA CODE |
| IDENTIFICATION OF EMPLOYEE THAT MADE THE LAST CHANGE TO THIS RECORD |
| DATE AND TIME OF LAST CHANGE TO THIS RECORD |
| APPLICATION ACCESS CONTROL ARRAY (specifies which programs or processes the person is allowed to execute) |

FIG. 29

| PERSONNEL PATIENTS 94 |
|---|
| DATE AND TIME THE ASSIGNMENTS WERE MADE |
| NUMBER OF PATIENTS ASSIGNED |
| AN ARRAY OF PATIENT IDENTIFIERS |

© 1988 Meditrol, Inc. (17 U.S.C. 401)

SYSTEM FOR DISPENSING DRUGS IN HEALTH CARE INSTITUTIONS

TECHNICAL FIELD OF THE INVENTION

The present invention pertains generally to computer machines and processes, and more particularly to a system for controlling the dispensing and inventory of medications in a health care institution.

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

BACKGROUND OF THE INVENTION

Modern medicine depends increasingly on the use of medications for the treatment and control of medical conditions. The use of drugs is particularly diverse and heavy in the health care institution environment, where the most serious medical conditions are treated. Today, the typical pharmacy needs to maintain a stock of approximately 3,000 to 5,000 different medications to meet routine demands.

The most important aspect of any institutional pharmacy operation is the delivery of medications from the pharmacy to the patient. Traditionally, prescriptions were filled by the institutional pharmacy and delivered to the dispensing station. As the use of drugs and the number of orders increased, however, this system became too slow in delivery time to the patient. Efforts to speed up delivery resulted in moving the drugs to where the patient was. This method was known as "floor stock." In the floor stock system, miniature pharmacies were created at each nursing station where the nurses interpreted the physician's order and dispensed the drugs without the aid of a pharmacist. This speeded up the drug delivery, but it created errors because the nursing staff lacked proper pharmaceutical training. These drug errors were of a magnitude that they became the primary reason to develop the "unit dose" system. In this system the institutional pharmacy made hourly deliveries to each nursing station.

By returning control of dispensing to pharmacy, error reduction was documented. Cost savings were such that the expense of the medication carts and other equipment were easily justified in concept. In practice, however, it soon became apparent that magnum increases in pharmacy staff were required to accomplish drug distribution every hour, on the hour. To solve this problem, institutions went to the "cart exchange" system. In the cart exchange system, the institutional pharmacy would stock a drug dispensing cart for each dispensing station on a periodic basis. Since most institutional administrators balked at increases in pharmacy staffing, the pharmacy was forced to reduced the number of cart deliveries to one delivery every 24 hours. This allowed the pharmacy to operate without the full staffing required by pure unit dose. It did, however, create a more serious problem of increasing medication errors. The cart exchange often required the pharmacy to guess what medications would be needed by any particular patient in the next 24 hours. Where a medication requirement was unanticipated, there was often an unacceptable delay in getting the needed medication to the patient. This often resulted in the "borrowing" of drugs from other patients, which in turn caused a loss of drug administration accuracy. The cart exchange system of unit dose drug distribution is basically an error producing method of handling drugs. Of the errors generated, 80 percent are errors of omission. This leaves 20 percent as errors of commission. The obvious reason for this is that pharmacy is required to load the carts 24 hours in advance. Since 30 percent of the total orders change daily, the carts have a built in error factor. Another problem is then created in that all of the drug omissions in the carts must now be supplied to the nursing stations. The majority of the new orders (omissions) are requested between $7 \geqq 8$ A.M., 12–1 P.M. and 7–9 P.M.

The average time required to deliver the first dose of medication ranges from 2.5 to 4 hours. If the first dose was to be given at 8 A.M. and it was not ordered until 7 A.M. then the chances of the patient getting a late dose or missing it entirely are very good.

Another problem has been the ability to provide 24 hour pharmacy service to remote hospitals, nursing homes, and clinics from a central location.

BRIEF DESCRIPTION OF THE DRAWINGS

FIG. 1 is a simplified block diagram of the system of the

FIG. 3 is a block diagram of the software modules according to the present invention;

FIGS. 4 through 30 are block diagrams showing the software modules, files and file structures of the software of the Applicant's system according to the present invention.

SUMMARY OF THE INVENTION

The dispensing system of the present invention solves all of the above noted problems of medication distribution in health care institutions. Medication errors due to mistakes in transcription are eliminated by allowing all orders to be inserted by pharmacists. Omission errors are eliminated by the dispensing cabinets at each dispensing station. Staffing needs are reduced by controlling all dispensing from a central pharmacy and by allowing pharmacy control from remote stations. Added to these advantages are automatic inventory control, automatic billing, automatic patient profiles, automatic medication administration reports, automatic hourly patient medication requirements report, automatic daily evaluation of medication due to discontinue, automatic drug-interaction and allergy warnings.

Other advantages are the elimination of narcotic counts, real-time inventory evalution, the ability to customize the hours and days to administer medication on a routine basis, the ability to limit the minimum and maximum times between doses on as needed medications, the ability to suspend all or specific orders for a patient for a variety of conditions, as well as the ability generate numerous administrative reports on demand.

DETAILED DESCRIPTION OF THE INVENTION

Figure 1:
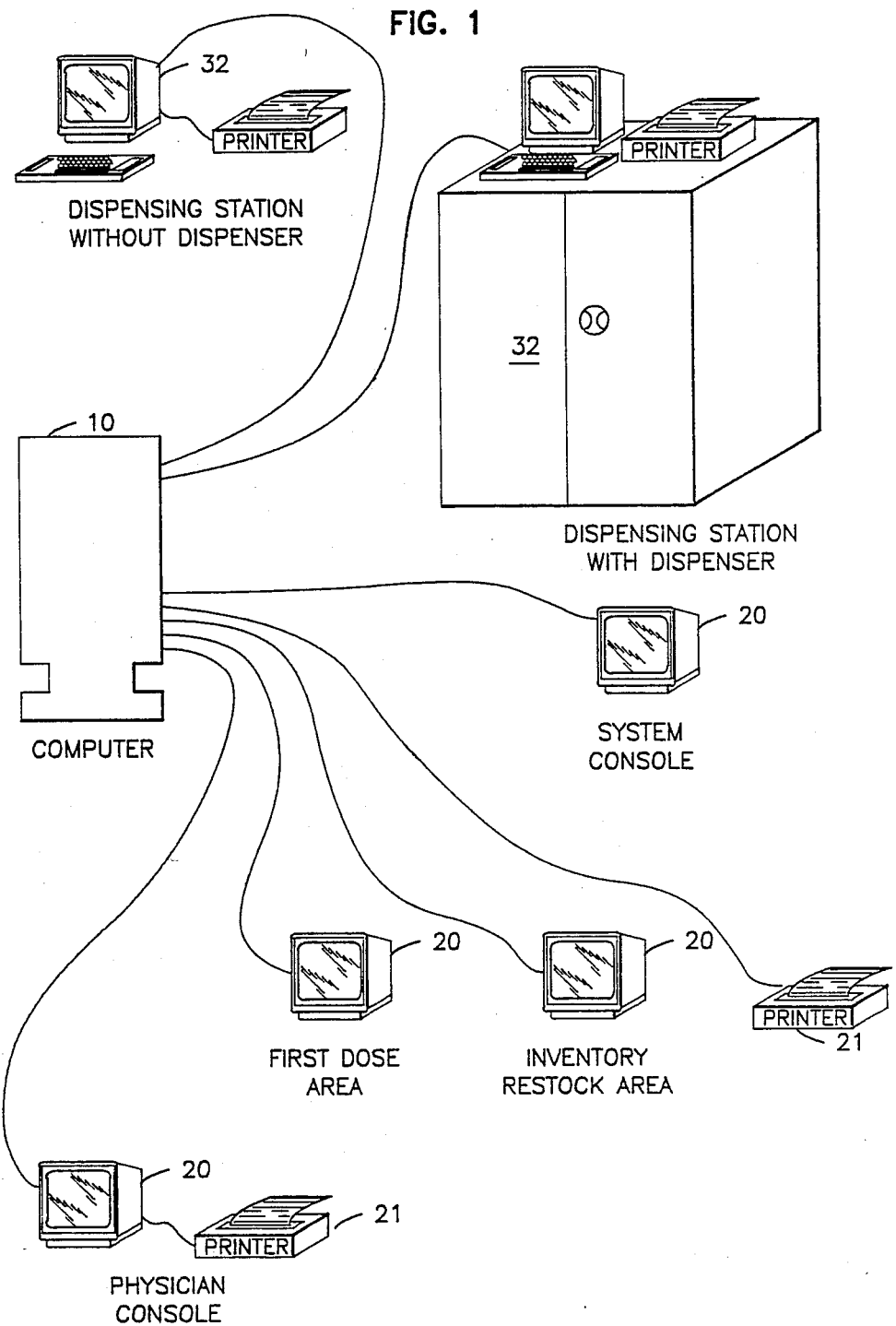

The medication dispensing system of the present invention as illustrated in FIG. 1, is implemented with a combination of hardware composed of a digital computer 10 which includes one or more centeral processing units, high speed instruction and data storage, on-line mass storage of operating software and short term storage of data, off-line long term storage of data, and a plurality of communication ports for the support of remote terminals; remote terminals encompassing video display units with keyboards 20, printers 21, and dispenser interfaces 32; software comprising the operating system, normally supplied by the computer vendor, and the application software which causes the hardware to perform the designated functions relating to medication distribution to patients and the accountability of the distribution. The system currently runs on any Data General processor which supports the AOS/VS operating system.

The hardware of the preferred system has a central computer 10 that is operatively connected to remote video display and keyboard entry units 20 used for information entry. Information entry includes patient information, all medication orders, inventory data and patient orders. The hardware of the system also provides the ability to perform information inquiry and modification, operating system control & application control. It includes one or more printers 21 in strategic locations to provide hardcopy information to institution personnel such as inventory control reports, patient records, medication labels & various other administrative reports.

Figure 2:
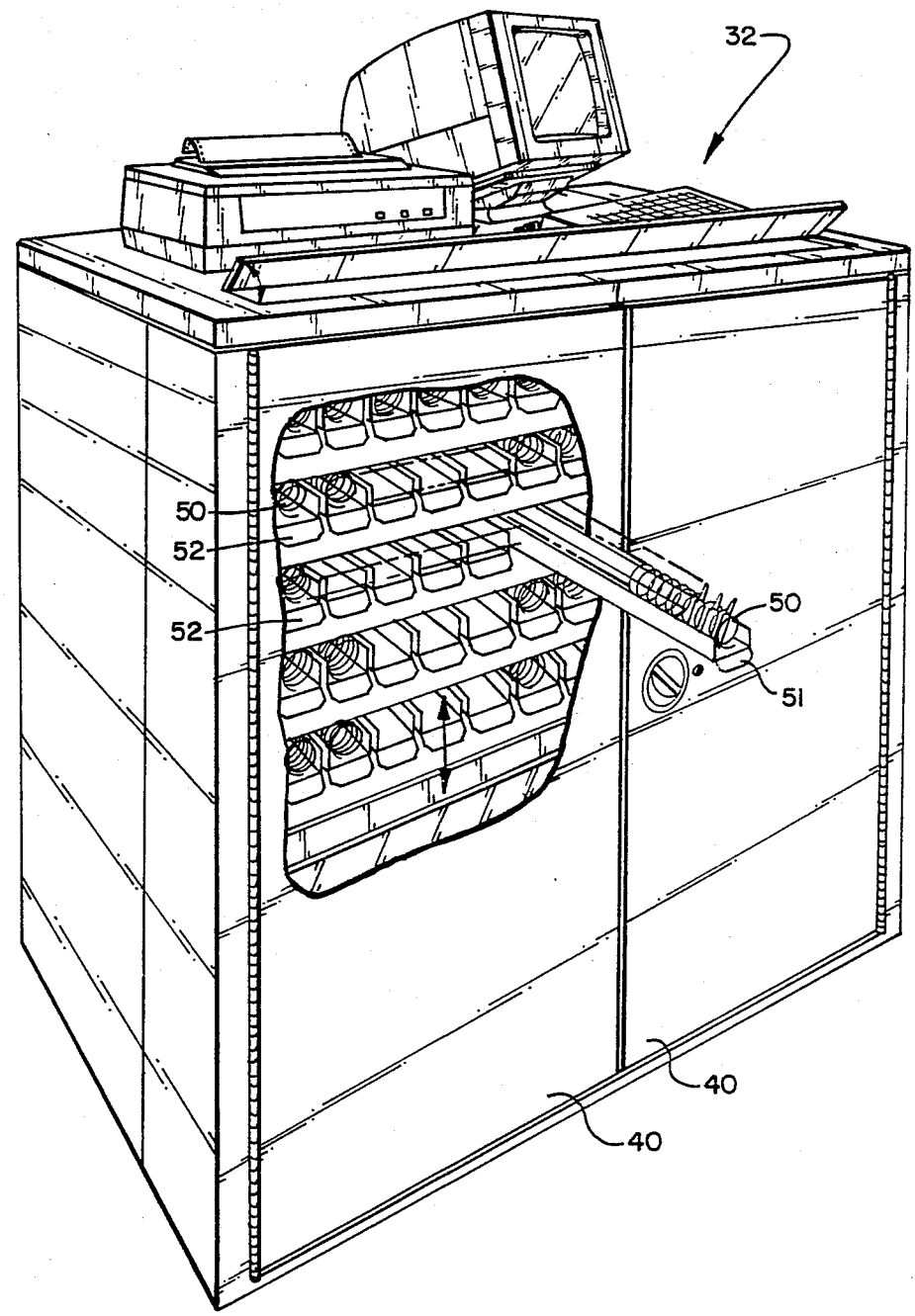
FIG. 2 shows a dispensing cabinet that can be used in the Applicant's system according to the present invention.

The hardware of the preferred system would include electro-mechanical dispensers 32, having video display units with keyboards 30, and with printers 21 that are multiplexed into the dispensers 32 interface. These dispensers are located at nursing stations and the dispensers 32 are operatively connected to the central computer 10. The dispensers 32 of the present system, shown in more detail in FIG. 2, are preferably unit dose dispensers in which the dispenser is responsive to control signals to dispense one unit dose package at a time. For instance, the dispenser 32 may employ a plurality of spiral carrier members 50 which can be selectively rotated to dispense a unit dose package. Preferably, the spiral drive member 50 is supported on a try 52, and the spiral member 50 is detachably coupled to a drive motor mechanism so that the tray members may be readily interchanged for restocking the dispenser 32. Another unit dose dispenser that could be used in the system is shown in U.S. Pat. No. 3,917,045.

The dispensers 32 of the preferred system have a software controllable, electrical interface that may receive data from the central computer 10. Logic circuits in the interface evaluate the data sent by the computer 10. This data may be categorized as; multiplexer instructions; dispenser operation commands; medication selection; data to be video displayed and/or printed. The interface contains a multiplexer that routes the data received to either the dispenser operations logic interpreter, the medication selector logic or to the external peripherals. The dispenser operator interpreter causes the dispenser to report it's status to the computer 10, lock and unlock the access doors 40 and to raise or lower the elevator if it is so equipped, etc. The medication selector logic causes the appropriate electrical device, such as a motor or solenoid to release a dose of a particular medication.

The interface also has the appropriate logic circuits to monitor various status conditions and to send this information to the computer. These status indicators may include, but not be limited to, such things as stocking access doors open/closed, medication access doors open/closed, elevator position, power failure, polling enabled/disabled, dispenser enabled/disabled & dispenser active/idle. The interface can send status messages to the computer 10 if solicited by the computer 10, if unsolicited (yet sensed by the interface), or during polling.

The polling messages are automatically sent to the computer 10 several times per minute. The primary purpose being to monitor the dispenser's operational condition. The software causes the computer 10 to keep track of the elapsed time between pollings and if it exceeds a prescribed length of time, the system will first attempt to resolve the problem itself. If this is not successful, it will notify the appropriate operational personnel of the problem. These problems will include but will not be limited to; loss of power to the dispenser, failure of communication lines (including telephone lines) between the computer 10 and the dispenser 32 or interface failure. In most instances, the computer 10 will rectify the problem once it has been made aware of it by the interface.

Reports that are created automatically or that are requested to be sent to a terminal, are held temporarily in spooling until the terminal is known to be in the idle condition at which time, the report is printed automatically.

The preferred dispensing station will have a dispenser 32 which contains a plurality of medications that may be automatically dispensed to authorized personnel on demand. No medications are dispensed without first being authorized by a physician.

In general, all patient orders can be divided into the catagories of being Routine or PRN. Routine medications are given on a periodic basis and at specified times. PRN medications may be given as the patient requires them, as long as certain limits on dosage and time interval are met. In both categories the strength of the medication, the preferred form and route of administration and other limiting conditions are entered for each. Once this has been entered into the computer 10, the system will automatically determine the stocking location and will either reserve the specific doses of medication in the appropriate dispensing cabinet 32 or inform the appropriate delivery area of the quantity of medications required to be delivered to that dispensing location.

The system provides for the automatic checking of a patient's medication order as it is being entered into the computer to warn of medication duplication, medications which are therapeutically alike and individual drugs which should not be administered in the same drug regime. Should such a warning appear, the person entering the order must decide if the new drug may be given. No new medication can be added to a patient's regime without this approval.

At the dispensing station, the system will automatically, every hour on the half hour evaluate each patient's orders and determine if the medication should be given during that hour. If so, this information will be printed on a report at that station. If a medication should have been given in the preceeding hour, and was not; the nurse will also be notified of that fact. If no patients required medications, this will also be printed.

The system will also schedule other medications that, for a variety of reasons, are not stocked in the cabinet 32; such as intravenous medications that will be needed by patients at a dispensing station. The lead time will be calculated and the appropriate labels produced to allow the medications to be prepared and delivered for use at the appropriate time.

Although the dispenser 32 is used primarily to dispense unit dose medications, it may control multi-dose and bulk packages such as creams, ointments, vials, etc., where the patient receives the initial package from the dispenser 32 and the unused portion is stored in the patient's drawer for subsequent use later. When the supply is exhausted, the nurse may request another package from the system. If the medication is stocked in the dispenser 32, it will be dispensed immediately. If it is not in the dispenser 32, the nurse will receive notification that the medication has been ordered from pharmacy. A message will be automatically printed on the pharmacy restock area 22 to inform them of the need from immediate delivery of the medication.

Should the dispenser 32 deplete it's supply of needed medications, the restocking personnel will automatically be notified (via a hardcopy report printed at the appropriate restocking station 22) of the drug needing restocking, the nurse will also be advised that the dispenser supply has been exhausted and that the restocking personnel have been informed. The nurse will also be informed of alternate dispensing locations, if any, that have the drug available.

The system will also automatically evaluate the time and dosage limits on every patient's orders on a daily basis. A report will be produced at each dispensing location that informs each physician of all of the orders that will be discontinued within the next 24 hours, if the orders are not renewed. The system also produces a report to inform the nurses of the orders that were discontinued by the system due to a limitation on number of days or on a maximum number of doses.

The dispensing system can also support dispensing locations that do not have mechanical dispensers, as shown in FIG. 1, but the stations must have, at least, a video display unit 30 with a keyboard and preferably a printer 21. At these stations either a floor stock or a cart exchange method of distributing medications may be employed. With the floor stock system, the system will monitor the drugs stocked at the station. It will schedule medications and maintain an inventory of current quantities, the usage and subsequent restocking if necessary. medications administration personnel (nurse) enters into the computer 10 the usage of each drug by each patient as it is administered; and thus receives most of the benefits that a station with a dispenser would receive. In stations that choose to use the cart exchange, the system maintains a patient drawer that will be stocked daily with the medications the patient has prescribed. With both of these methods the system will automatically produce a report every hour on the half hour (just as with stations with dispensers) that will indicate which patient needs medications and what the medications are to be. In all methods, the system maintains an inventory of the medications at the dispensing locations. The system will insure that all subsequent day medications are stocked at the dispensing locations. First dose medications are also available in most cases at stations that have either a mechanical dispenser or employ the floor stock method because the system maintains a history of drugs used at each station and stocks medications at the station by using an equation that considers usage history, cost of medication, space availability, etc. With the cart exchange method, this is not possible because only the medications that a patient is currently using are stocked in the patient's drawer in the cart.

SYSTEM DATA BASE DEFINITIONS

The database is illustrated by FIGS. 4–30. FIG. 4 describes the files contained in the database. FIGS. 5–30 identify the data specific to each file. The system has a file that contains a record for each unit of the institution or each unit of each institution in the multi-institution environment. This file will be referred to as the INSTITUTION MASTER 70 which contains the following elements:

1. Institution reference code
2. Description field used primarily for report titles The system has a file that contains a record that defines each bed in the system which will be referred to as the ROOM BED file 71 and contains the following elements:

1. Room-bed definition code
2'. Institution reference code for the bed
3. The station reference code for the bed
4. Identification of the patient currently occupying the bed The system has a file that contains a record for each station in each institution. A station is defined as any location within the institution that has a terminal. This includes nursing stations within wards, data entry locations within pharmacy, inquiry locations for doctors, locations with printers, etc. This file will be referred to as the STATION MASTER 72 which contains the following elements:

1. Institution reference code for this station
2. Station reference name
3. Station type indicator (nursing, pharmacy, inquiry, system, etc.)
4. Operational status indicator (online, offline, training)
5. Dispensing method at nursing stations (indicates whether the station is employing mechanical dispensers, a cart exchange, or a floor stock system)
6. Computer console port identification
7. Terminal type indicator (CRT, Printer, or combinations)
8. Printer connection indicator (none, CRT, auxiliary port, direct connect to the computer, or dispenser multiplexer port)
9. Printer model indicator (Decwriter, Inkjet, etc)
10. Number of lines to space up the paper upon completion of printing
11. Timeout factor, used to return the terminal to an idle state if it is left unattended
12. HELLO character, used to certify the transmissions with each dispenser
13. Dispensing station number
14. First dose inventory site identification
15. Restock inventory site identification The system contains a file for each ward that will be referred to as the STATION DRUG file 73. The file contains one record for each drug stocked at the station. This file contains the following elements:

1. Identification of the drug
2. Number of patients being serviced by this station that require this drug on a routine (RTN) schedule
3. Number of doses needed for the RTN medications at this station
4. Number of patients being serviced by this station that require this drug on an as needed (PRN) basis 5. Number of doses needed for the PRN medications at this station
6. Current quantity of the drug at the station
7. Minimum quantity to maintain at the station
8. Date and time of last usage
9. Retention factor which is one of the parameters used in the equation to compute the unused elapsed time necessary before the remaining quantity of the drug is returned to the pharmacy inventory stock The system contains a file for each ward that has a mechanical dispenser that will be referred to as the STATION SLEEVE file 74. The file contains one record for each slot (a space that can accomodate one sleeve) in the dispenser. This file contains the following elements:
1. Identification of the drug currently in the sleeve, if any
2. Current quantity of doses of the drug in sleeve
3. Date and time of last usage of the sleeve
4. Quantity of doses in the sleeve when installed
5. Date and time when the sleeve was installed
6. Quantity of doses in the sleeve at the last cabinet refill
7. Slot parameters contain information such as slot height and horizontal space limitations that must be considered when installing a new drug in the dispenser
8. Current sleeve type in this slot The system has a file which contains a record for each type of sleeve which a dispenser may use. This file will be referred to as the SLEEVE SIZE file 75 and contains the following elements:
1. Sleeve identifier code
2. Sleeve color (the sleeves may be color coded to coincide with the sleeves capacity)
3. Sleeve capacity (the number of doses the sleeve is capable of holding)

The system contains a file which is used to maintain the inventory in the dispensers. The first file is used to define refill routes and will be referred to as DISPENSER ROUTES 76. The file contains the following elements:
1. Route number
2. Route title
3. In-service indicator
4. Array defining the hours of the week for scheduled reloading of the dispensers on this route
5. Array identifying the stations on the route The system has a file which contains a record for each drug form which is currently recognized by the system. This file will be referred to as the FORM DICTIONARY file 77 and contains the following element:
1. Form code (tablet, capsule, injection, etc.)

The system has a file which contains a record for each pre-defined drug administration schedule for routine (RTN) medications. This file will be referred to as the FREQUENCY CODES file 78 and contains the following elements:
1. Institution reference code
2. Frequency code (QID, TID, BID, AM, etc.)
3. Scheduled hours for administration The system has a file which contains a record for each route of administration. This file will be referred to as the ROUTE DICTIONARY file 79 and contains the following information:
1. Route of administration (oral, topical, rectal, etc.)

The system has a file which contains a record for each type of allergy. This file will be referred to as the ALLERGY DICTIONARY file 80 and contains the following elements:
1. Group identification code
2. Description of Allergy The system has a file that defines all of the drugs under control of the pharmacy. The file contains a record for each drug that is unique in generic name, strength, form, and route of administration from all other drugs in the system. This file will be referred to as the DRUG MASTER 81 and contains the following elements:
1. Generic name
2. Currently used brand (trade) name
3. Strength of the package
4. Form of medication
5. Preferred route of administration
6. Sleeve definition parameters (dimensions of package & preferred sleeve)
7. Maximum number of days that an order may be written for
8. National drug code (NDC number)
9. Controlled substance classification code
10. Therapeutic classification code
11. Formulary indicator
12. Dispense location (Dispenserable, Pharmacy delivery, Floor stock, etc.)
13. Issue package type (Unit dose, Multi-dose, Bulk)
14. Standardized administration information and warnings
15. Pricing information
16. Inventory quantity The system has a file that contains the generic drug names. This file is maintained in a sorted sequence for name look-up. The file will be referred to as the DRUG GENERIC file 82 and each record has the following elements:
1. Generic drug name
2. Therapeutic equivalence code for this drug
3. Drug-drug interaction code for this drug
4. Array of drug-drug interaction codes that interact with this drug The system has a file that contains the brand drug names. This file gives the system the ability to have several suppliers of the same drug and allow the user the ability to reference the drug with each suppliers unique brand name. The file is maintained in a sorted sequence for name look-up. The file will be referred to as the DRUG BRAND file 83 and each record has the following elements:
1. Brand (trade) name
2. Corresponding generic name The system has a file that contains a record that defines each therapeutic classification and will be referred to as the DRUG THERAPEUTIC EQUIVALENT file 84. Each record in the file will contain the following elements:
1. Therapeutic code
2. Description of the classification The system has a file that contains the ordering information necessary to maintain the pharmaceutical inventory. The file will be referred to as the DRUG ORDER file 85 and each record will contain the following elements:
1. Drug identification
2. Re-order point in issue units
3. Number of issue units per order unit
4. Order unit's definition
5. Default order quantity in order units 6. Primary supplier identification
7. Primary supplier's drug order code
8. Secondary supplier's identification
9. Secondary supplier's drug order code
10. Date the last order was placed
11. Reference number of the last order
12. Date the last order was received
13. Quantity received in the last order
14. Quantity on order in issue units The system contains a file that defines all of the inventory stocking sites and the times of operation. This file will be referred to as INVENTORY SITES 86 and each record will contain the following elements:
1. Site identification number
2. Site name
3. Standard hours of operation of each day of the week
4. Holiday hours of operation
5. Station name where restock notices are printed
6. Station name where reports are printed
7. Alternate site to refer to when this site is not in operation
8. Number of the site that restocks this site The system contains a file that has a record for each record in the DRUG MASTER file when contains restocking information for each of the inventory sites. This file will be referred to as DRUG INVENTORY QUANTITY 87 and will contain the following elements:
1. Inventory site number
2. Current quantity at the site
3. Reorder point. (The minimum quantity allowed without restocking)
4. Preferred restocking quantity The system contains a file with one or more records for each doctor at the institution who chooses to create standardized (canned) orders for their patients. A separate record is created in this file for each canned order a doctor wants in his regime. This file will be referred to as CANNED MASTER 88 and each record will contain the following elements:
1. Doctor identification
2. Drug identification
3. Canned order numbr
4. Drug dosage
5. Order type (PRN, RTN, etc.)
6. Frequency code
7. Number of days to run
8. Hold status The system contains a file with a record for each patient which will be referred to as the PATIENT MASTER 89 which has each of the following elements:
1. Identification Number (ID)
2. Name
3. Date of Birth
4. Personal data (height, weight, sex, etc.)
5. Admitting date and time
6. Attending physician
7. Primary nurse
8. Location (institution, ward, room, bed)
9. Date and time of last bed assignment
10. Discharged code (Released, Deceased, Transferred, etc.)
11. Description of Diagnosis
12. Description of Allergies
13. Global hold indicators (holds for all orders for this patient)

The system contains a file with a record for each patient order. This file will be referred to as the PATIENT ORDER file 90 and will contain the following elements:
1. Patient Identification
2. Drug name (generic and brand)
3. Drug form
4. Route of administration
5. Actual dosage
6. Frequency code
7. Quantity of packages to issue per medication
8. Date and time of first dose
9. Date and time of last renewal
10. Date and time the last dose was received
11. Number of doses received
12. Date and time the last dose was issued
13. Number of packages issued
14. Hold indicators (NPO, Surgery, General, etc)
15. Hold Start and Stop date and time
16. Discontinued indicator
17. Issuing package type (Unit dose, Multi-dose, Bulk)
18. Type of medication regime (Routine, PRN, etc)
19. Receive from location (Dispenser, Cart, Floor stock, etc)

On RTN records:
20. Array of 24 elements used to indicate the scheduled hours of administration
21. Interval indicator (Every day, Even days, Odd days, Specific days, etc)

On PRN records:
22. Estimated usage per day
23. Minimum hours between doses
24. Maximum hours between doses
25. Maximum days to administer limit
26. Maximum doses to administer limit
27. Start indicator
28. Administration information and warnings
29. Therapeutic Equivalent code
30. Identification of ordering physician
31. Identification of entry and modification personnel
32. Price of the medication
33. Drug-drug interaction code The system has a journal type file 91 for each patient that contains a record for each pharmacy related transaction. This file will be referred to as the PATIENT HISTORY file and contains each of the following elements:
1. The date and time of the transaction
2. Transaction record type (drug charge, drug credit, bed change, etc)
3. Identification of personnel associated with this transaction
4. Drug identification
5. Quantity of drug
6. Price of medication
7. Patient identification
8. Patient location The system has a journal type file for each day that contains a record for each pharmacy related transaction. This file will be referred to as the MEDICATION HISTORY file 92 and contains each of the following elements:
1. Date and time of the transaction
2. Transaction record type (drug charge or drug credit)
3. Identification of personnel associated with this transaction 4. Drug identification
5. Quantity of drug
6. Dispensing location (Dispenser, Pharmacy, etc)
7. Price of medication
8. Patient identification
9. Patient location The system contains a file with a record for each employee of the facility that will have access to the system. The file will be referred to as PERSONNEL MASTER 93 and will contain the following elements:
1. Identification number (system assigned)
2. Full name
3. Department code (Pharmacy, Nursing, etc)
4. Active indicator
5. Password
6. Institution that employee is working in
7. Employee title (Head, Supervisor, Staff, etc)
8. Work area code
9. Identification of employee that made the last change to this record
10. Date and time of last change to this record
11. Application access control array (specifies which programs or processes the person is allowed to execute)

The system contains a file that is record locked with the PERSONNEL MASTER that contains the patient identifiers for all of the patients that are assigned to the nurse for the shift. This file will be referred to as PERSONNEL PATIENTS 94 and will have the following elements:
1. Date and time the assignments were made
2. Number of patients assigned
3. An array of patient identifiers The system has a file that contains records with parameters for automatic scheduling of periodically executed programs. The file will be referred to as the SCHEDULER file 95 and will contain the following elements:
1. Reference name of event The time specifiers used to cause execution of the program. . .
2. MOH—Minute Of Hour
3. HOD—Hour of Day
4. DOW—Day of Week
5. DOM—Day of Month
6. MOY—Month of Year
7. Program name with execution arguments

INITIALIZATION

Before the system can be used, a number of the previously mentioned files must be "built" by the institution staff with the coordination of installation staff. Software routines are provided to accomplish this and, for the sake of brevity, are not discussed herein. The files which need to be created are as follows:
HOSPITAL LOCATION FILES
  INSTITUTION MASTER
  STATION MASTER
  ROOM BED
DISPENSING CONTROL FILES
  STATION DRUG
  STATION SLEEVE
  DISPENSER ROUTES
  DISPENSER ROUTE STATIONS
PERSONNEL FILES
  PERSONNEL MASTER
  PERSONNEL PATIENTS
AUTOMATIC PROCESS EXECUTION FILES
  SCHEDULER
DRUG RELATED FILES
  DRUG MASTER
  DRUG GENERIC
  DRUG BRAND
  DRUG THERAPEUTIC EQUIVALENT
  FORM DICTIONARY
  ROUTE DICTIONARY
  ALLERGY DICTIONARY
  SLEEVE SIZE
  FREQUENCY CODES
  INVENTORY SITES
  DRUG INVENTORY QUANTITY

CREATION OF DATA BASE FILES

The first sequence would be to create the PERSONNEL TITLES and PERSONNEL MASTER 93 files, followed by the creation of the INSTITUTION MASTER 70, STATION MASTER 72 and ROOM BED 71 files. This sequence would be followed by the creation of the drug related files: FORM DICTIONARY 77, ROUTE DICTIONARY 79, DRUG THERAPEUTIC EQUIVALENT 84, SLEEVE SIZE 75, DRUG BRAND 83, DRUG GENERIC 82, FREQUENCY CODES 78, and DRUG MASTER 81 files.

An initial dispensing station stocking plan is then developed based on expected needs at each station, and the necessary STATION DRUG 73 and STATION SLEEVE 74 files are prepared. Dispenser routes are established, and corresponding records are created in the DISPENSER ROUTES 76 and DISPENSER ROUTE STATIONS files. Also, drug inventory sites are chosen and the INVENTORY SITES file 86 and its corresponding DRUG INVENTORY QUANTITY files 87 are created.

SYSTEM-MAINTAINED FILES

Several files are continuously maintained during normal system usage. These files are:
PATIENT MASTER
PATIENT ORDER
PATIENT HISTORY
MEDICATION HISTORY
DRUG ORDER When a new patient is admitted to the health care institution, a new record is created for the patient in the PATIENT MASTER file 89, the bed assignment is stored in the ROOM BED file 71, and a PATIENT HISTORY file 91 is created. Pharmacy is notified each time a patient is prescribed a new medication and a new record is created in the PATIENT ORDER file 90. A patient will never receive a medication unless it is first entered into this file as being a valid drug for the patient. A patient usually will have a plurality of records in this file, since a record is created for each drug that is prescribed for the patient.

The DRUG ORDER file 85 stores data necessary to maintain inventories at the restocking stations. This data includes supplier codes, order quantities, previous order date, last shipment received date, etc..

The system maintains two seperate journal type files that record the dispensing data. One file, PATIENT HISTORY 91, contains all of the records for the patient per admission to the institution. The other file, MEDICATION HISTORY 92, is created for each day and contains the dispense data for all patients in the hospital for that day.

JOURNAL FILE USES

The PATIENT HISTORY file 91 and the MEDICATION HISTORY file 92 are used for billing information, order administration review, drug utilization analysis, etc.

SYSTEM PROGRAMS

Figures 3, 30:
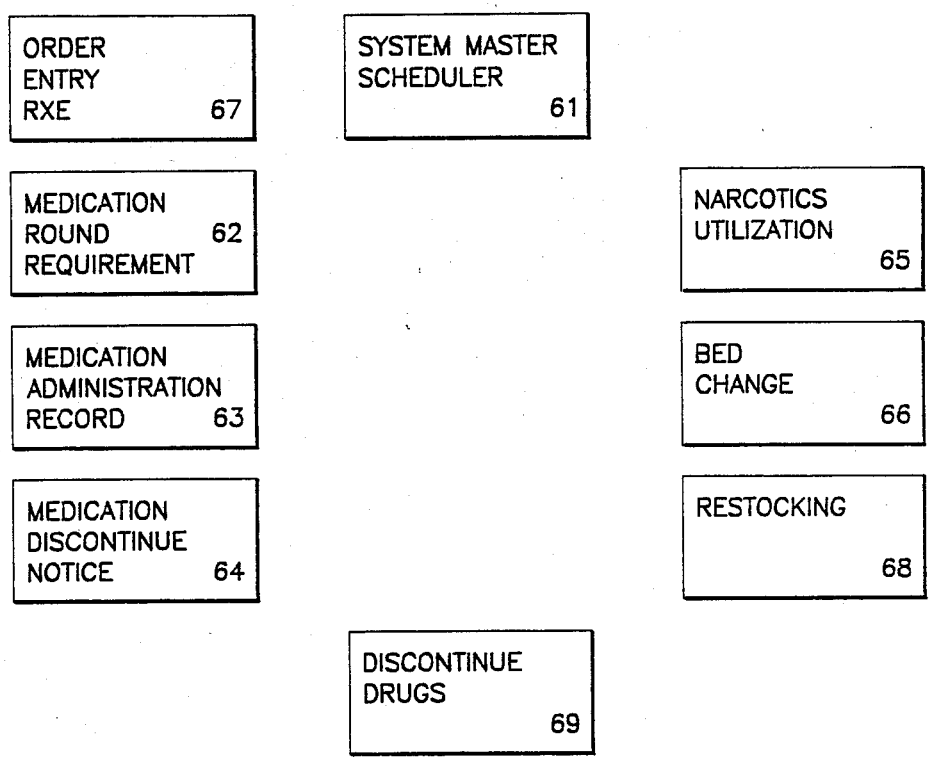

The following programs, illustrated in FIG. 3, are provided for general system support:
  System Master
  Medication Round Requirement
  Medication Administration Record
  Medication Discontinue Notice
  Discontinue Drugs
  Narcotics Utilization
  Bed Change
  Restocking

SYSTEM MASTER/SCHEDULER

The System Master (MST) program 61 scans the STATION MASTER file when the system is booted and begins execution of the support programs required at each station. The MST program is responsible for maintaining a "a state of operation" at all of the stations. It constantly monitors all program termination notices and takes appropriate actions (such as restarting a process if it terminates prematurely) if necessary. The MST program is responsible for the running of all "scheduled" programs [SCHEDULER] and also coordinates the spooling of reports.

MEDICATION ROUND REQUIREMENTS

The Medication Round Requirements (MRR) program 62 is set up to run automatically at each dispensing station once each hour on the half hour [SCHEDULER]. For each patient assigned to a bed in the ward, the program performs the following:
  Scans all of the patient's orders to determine which orders are scheduled to be administered during the next administration round.
  This includes the following:
  Any regularly scheduled medications [PATIENT ORDER:20&21]
  Any STAT medications [PATIENT ORDER:27]
  Any PRN medications that have exceeded their maximum time between doses [PATIENT ORDER:24]
  Any orders which were scheduled to be administered during a previous medication round but were not indicated as having been withdrawn for administration [PATIENT ORDER:20&21]
  This excludes the following:
  Any orders in which the maximum doses allowed has been reached [PATIENT ORDER:26]. If this occurs, the discontinue notice is included on the report.
  Any orders which have a "hold" placed on them [PATIENT ORDER:14&15]. In this case, an explanation of the type of hold (oral, general, etc.) that is in place and the duration of the hold is given.

The report is printed at the nursing station associated with each ward and contains the following elements:
  Report identification
  Patient identification [PATIENT MASTER:1&2]
  Room-Bed location [PATIENT MASTER:8]
  Drug to be administered [PATIENT ORDER:2]
  Drug dosage, form, and route [PATIENT ORDER:5&3&4]
  The drug's dispensing location [PATIENT ORDER:19]

NOTE: References to data base record fields are indicated using the notation [FILE NAME: #], where FILE NAME is the file being referenced (as previously defined in the Data Base File Description section), and # is the element being referenced in this file. Multiple elements are also referenced using this same method, [FILE NAME: #1,#2,etc.].

If the drug is to be administered as a PRN drug [PATIENT ORDER:8], "PRN" is indicated along with the date and time that the last dose was administered [PATIENT ORDER:10], and the maximum time that should be allowed between doses [PATIENT ORDER:5]
  Any special instructions that were included on the patient's order [PATIENT ORDER:28]
  If this is the last normally scheduled dose to be given [PATIENT ORDER:23&24], then the nurse is informed of this.

MEDICATION ADMINISTRATION RECORD

The Medication Administration Record (MAR) program 63 is set up to run automatically once each day at the institution defined time [SCHEDULER] for all patients in all wards, and may also be run on demand for a specific patient. For each patient in each ward, the program scans all of the patient orders [PATIENT ORDERS] to determine all of the scheduled drugs for the following day and prints a report which has the following elements:
  Station Identification [STATION MASTER:1&2]
  Patient Identification [PATIENT MASTER:1&2]
  Date and time the report was produced
  Room-Bed location [PATIENT MASTER:8]
  Scheduled drugs by category (RTNs, PRNs, OPs) [PATIENT ORDER:18]
  For each drug in the above category:
    Drug to be administered [PATIENT ORDER:2]
    Dosage, Form, Route, and Frequency [PATIENT ORDER:5&3&4&6]
    Days before order expires [PATIENT ORDER:25]
    Any special instructions [PATIENT ORDER:28].

The MAR is designed to give nurses a listing of what drugs are needed for each patient for the following day. It will become the permanent record of drug administration at the end of each day when it will contain the nurse's initials for each time a medication was administered and the nurse's signature on the form.

MEDICATION DISCONTINUE NOTICE

The Medication Discontinue Notice (MDN) program 64 is set up to run automatically once each day at an institution defined time [SCHEDULER], preferably early in the morning. For each doctor at each ward, the program scans the patient orders to determine which orders will be automatically discontinued due to dosage [PATIENT ORDER:26] or duration [PATIENT ORDER:23] limits being reached within the next 24 hours, if not renewed and produces a report at the nursing station for each ward which contains the following elements:
  Report title
  Station Identification [STATION MASTER:1&2]
  Date and time the report was produced Doctor's name [PATIENT ORDER:30 & PERSONNEL MASTER:1&3]
Patient's name [PATIENT ORDER:1]
Patient's location [PATIENT MASTER:8]
Drug which is to be discontinued [PATIENT ORDER:2]
Drug form and dosage [PATIENT ORDER:3&5]
Last renewel date [PATIENT ORDER:9]
Number of doses of the medication which were administered [PATIENT ORDER:11]

The MDN is intended to give the nurses at each ward sufficient time to notify physicians of any drugs which a patient may need but are about to be discontinued.

DISCONTINUED DRUGS

The Discontinued Drug (DCD) program 69 is set up to automatically run once each day at a institution defined time [SCHEDULER]. For each patient in each ward, the program scans the patient orders and determines if an order has run its specified maximum days [PATIENT ORDER:25] (based on its renewal date) [PATIENT ORDER:9] or has reached a specified number of doses [PATIENT ORDER:26]. If it has, then the DC'ed field in the patient order record is "set" [PATIENT ORDER:16] which will signify that the order has been discontinued. This program updates all patient orders and produces a report similar to the Medication Discontinue Notice (MDN) report.

NARCOTICS UTILIZATION

The Narcotics Utilization (NARC) report 65 is set up to run automatically at the nursing station for each ward once each day at the institution defined time [SCHEDULER]. It is primarily used for monitoring the usage of controlled substances and contains the following elements:
  Report title
  Station Identification [STATION MASTER:1&2]
  Date and time the report was produced
  Drug name, dosage, and form [MEDICATION HISTORY:1]
  Drug class [MEDICATION HISTORY:4]
  Date and time the drug was administered [MEDICATION HISTORY:1]
  Patient's name [MEDICATION HISTORY:8]
  Administering nurse's name [MEDICATION HISTORY:3]
  Charge code (CHarge, CRedit) [MEDICATION HISTORY:2]
  Dispensing location (dispenser, pharmacy, etc.) [MEDICATION HISTORY:6]

BED CHANGE

The Bed Change program 66 permits patients to be moved to different beds in an institution. Two types of bed changes are performed:
  Bed changes within the same station: This change is reflected in the room bed current occupant [ROOM BED:4], patient location [PATIENT MASTER:8], and date and time of last bed assignment [PATIENT MASTER:9]. A patient history record indicating that a bed change has taken place is also appended to the patient's current PATIENT HISTORY file [PATIENT HISTORY:2].
  Bed changes to different stations: Again, changes are affected in the room bed current occupant [ROOM BED:4], patient location [PATIENT MASTER:8], date and time of last bed assignment [PATIENT MASTER:9], and a patient history record indicating that a bed change has taken place is also appended to the patient's current PATIENT HISTORY file [PATIENT HISTORY:2]. Medication requirements (# of patients at this station requiring this drug [STATION DRUG:2,4] and # of doses needeed of this drug [STATION DRUG:3,5] at the previous station must be de-allocated and then re-allocated at the patient's new station. A report is printed at the patient's previous station informing the transferring personnel to retrieve all Bulk and pharmacy delivered medications [PATIENT ORDER:17] at that station and to transfer them along with the patient to the new station. A report may also be printed at the patient's first dose stocking area [STATION MASTER:14] informing personnel to stock the new station with the appropriate quantity of medication needed at the new station. This report is printed only if the new station doesn't currently stock the required quantity. The quantity of medication needed at the new station is determined by the type of medication (RTN, PRN, etc. [PATIENT ORDER:18]. If the medication is a routine medication (RTN), the quantity is computed based on the frequency code [PATIENT ORDER:6], the scheduled hours of administration [PATIENT ORDER:20], the interval indicator [PATIENT ORDER:21], and the next scheduled restock [DISPENSER ROUTES:4]. If the medication is a PRN medication, the quantity is computed based on the date and time the last dose was received [PATIENT ORDER:10], the minimum hours between doses [PATIENT ORDER:23], and the estimated usage per day [PATIENT ORDER:22].

PHARMACY/RXE

Pharmacy, in general, is given access to system programs which perform the following functions through program RXE:

ADD CANNED ORDERS

Canned orders may be added to a patient's order file. Doctors may create their own "standardized orders" which allows easy entry of a patient's drug orders. Canned orders are stored in the CANNED MASTER file.

CHANGE ORDERS

Patient's current orders may be changed. Choices are made as to the types of orders to be changed (RTN, PRN, etc.) [PATIENT ORDER:18] and the order status to be changed (Active, Held, DC'ed, etc.). All of the patient's orders that meet the previously chosen specifications (if any) are then displayed from the newest to the oldest. Orders to be changed are chosen by item number. Changes may be made to the Date Renewed file [PATIENT ORDER:9], Hold Status [PATIENT ORDER:14], Hold Start and Stop Date and Time [PATIENT ORDER:15], and the Actual Dosage [PATIENT ORDER:5].

ADD ORDERS

An order can be appended to the patient's order file. As a new order is added, four levels of drug interactons are identified. These are:
  Drug order duplications Drugs that are in the same pharmacologic-therapeutic class [DRUG GENERIC:2]
Drug-drug interactions [DRUG GENERIC:3]
Allergic reactions that might be expected [ALLERGY DICTIONARY:1]

The "Add" routine may be exited from if any of the drug interactions are displayed. The program displays all available dosages of the chosen drug [DRUG MASTER:3] and the quantity available [STATION DRUG:6] at the patient's current nursing station. The desired dosage is then selected [PATIENT ORDER:5] along with the type of drug order being entered (PRN, RTN, Pre-Op, etc.) [PATIENT ORDER:18]. For all order types, the following must be entered:

Actual Dosage: This field specifies the actual dose of the medication. In most cases this will be the same as the issuing package but in some cases it will specify either a fraction of the issuing package such as a "1 gram"of a 2 gram table or multiple such as 650 mg when the issuing medication package only contains 325 mg. [Patient Order:5]

Packages/Issue: The number of packages to issue per dose is entered in this field [PATIENT ORDER:7].

Issue Stat: A YES in this field [PATIENT ORDER:27] indicates to the dispensing program that a dose is needed immediately..

First Dose D&T: This field [PATIENT ORDER:8] specifies the earliest possible date and time that a dose of the medication may be administered.

Maximum Doses: If the number of doses of this medication is to be limited, then the maximum number is entered here [PATIENT ORDER:26].

Holds: There are many situations where the order is to be suspended for a period of time. There are several holds defined in the system such as NPO which is for holding medication that are administered by mouth, SURGERY which suspends the medication until the patient has a bed change from surgery to a bed, EVENT which suspends the medication until a defined event has occurred such as discontinuing of another order, and GENERAL which will simply suspend the medication [PATIENT ORDER:14]. The hold start date and time is but the removal date and time is optional [PATIENT ORDER:15].

Auto Stop Days: The institution may set a default automatic stop for each drug [DRUG MASTER:7] which may be selected or overridden as appropriate [PATIENT ORDER:25].

Price/Package: The price for the drug is retrieved from the drug master file [DRUG MASTER:15] and may be overridden as appropriate [PATIENT ORDER:32].

Send Qty: If sufficient stock to fill the order doesn't exist at the dispensing station [STATION DRUG:2&3&4&5&6], the number of packages which must be delivered to the nursing station to meet the requirements until the next scheduled restocking of the nursing station [DISPENSER ROUTES] is displayed. If this quantity is greater than zero, the system will cause a message to be printed at the first doses inventory site [STATION MASTER:14] with appropriate patient and drug information.

Information: Any warnings or administration information that the nurse needs to be aware of each time the drug is referenced may be entered in this field [PATIENT ORDER:28]. The institution may define default information in the drug master file [DRUG MASTER:14].

Ordered By: The identification of the doctor who wrote the order is entered in this field [PATIENT ORDER:30].

RTN ORDERS

For RTN type orders, the following data is also requested:

Frequency Code: Most institutions will have a predefined list of mnemonics that represent standard hours of drug administration [FREQ CODES]. If a predefined regime is available, it is entered in this field [PATIENT ORDER:6] and the default hours of administration are entered [PATIENT ORDER:20] automatically from the frequence code file [FREQ CODES:3] otherwise, the hours of administration must be manually specified [PATIENT ORDER:20]. In either case they may be customized to the specific order by specifying that certain hours are to be skipped the first time and that other hours are to be scheduled only once.

Issue on Days: The system has the ability to schedule medications [PATIENT ORDER:21] on a variety of regimes:
Every day,
Specific days of the week,
Even numbered days only,
Odd numbered days only,
To skip a specific number of days between doses,
A specific day of each month.

PRN ORDERS

For PRN type orders, the following data is also required:

Min Hours/Dose: This field [PATIENT ORDER:23] contains the optional minimum number of hours that must elapse between doses. The system will only dispense subsequent doses of the medication if the specified number of hours has elapsed or the STAT indicator is set [PATIENT ORDER:28].

Max Hours/Dose: This field [PATIENT ORDER:24] contains the optional number of hours that can elapse before the nurse is reminded to administer the medication.

Subsequent days: This field [PATIENT ORDER:22] contains an estimate of the number of doses per day that the patient requires. This is used in calculating the drug stocking requirements at the dispensing station.

RESTOCKING PROGRAMS

There are several programs 68 provided which calculate restocking needs at dispensing stations and create restocking plans. These are:
Dispenser Requirements Report
Dispenser Loadfile Entry
Print Loadsheets and Labels
Dispenser Station Loading Report
Dispenser Update
Dispenser Restock Route Maintenance
Dispenser Sleeve Editor

DISPENSER REQUIREMENTS REPORT

The Dispenser Requirements Report (REQ) computes the sleeve requirements for the next restock period. The report accomplishes the following:

Scans all of the patient orders for each station to compute the number of PRN and RTN doses needed [PATIENT ORDER:18,22] during the next restock period [DISPENSER ROUTES:4]. This data is used to build the DISPENSER NEEDS file.

Scans the STATION DRUG file to determine the current quantity [STATION DRUG:6] of doses available at that station, and determines if this quantity will be adequate for the next restock period or if a drug restock on that medication is required.

Determine whether the drug has recently been used [STATION DRUG:8]. The program determines a maximum time interval to allow a sleeve to be maintained in the dispenser if it hasn't been used. This invterval is based on a "retention factor" which is stored in each station's drug file [STATION DRUG:9]. The retention factor's value determines how long this time interval is. If the drug hasn't been dispensed within the determined interval, then it is scheduled to be removed.

If a medication is needed which isn't currently available at the station, the program scans the STATION SLEEVE file [STATION SLEEVE:1] for an available slot. The DRUG MASTER file contains sleeve loading codes which indicate the type of sleeve to be used for the drug [DRUG MASTER:6].

The report contains the following elements:
Report title
Refill route and station name [STATION MASTER:2]
Date and time of the report
List of drugs currently in the station [STATION DRUG:1]. For each drug at the station, the report lists:
Drug identification code [STATION DRUG:1]
Drug name [DRUG MASTER:1,2]
Drug dosage and form [DRUG MASTER:3,4]
Sleeve size needed for this drug [DRUG MASTER:6]
Current quantity at the station [STATION DRUG:6]
Expected number of doses needed during the next restocking period [PATIENT ORDER:6,7,8,18,20,21,22,23,24,25,26]
The dispenser quantity expected at the time of the scheduled restock [STATION DRUG:3,5,6]
The number of RTN doses of this medication per number of patients using this drug as a RTN medication [STATION DRUG:2,3]
The number of PRN doses of this medication per number of patients using this drug as a PRN medication [STATION DRUG:4,5]

DISPENSER LOADFILE ENTRY

The Dispenser Loadfile Entry (LDE) program may be used to override the restocking requests made by the REQ program. REQ will compute a recommended number of doses to refill in each sleeve [DRUG INVENTORY QUANTITY:4]. This recommended number will be the actual number of doses that will be placed in the sleeve unless the LDE program is used to override this value. The LDE program can also be used to load anticipated drug needs.

INVENTORY CONTROL

The system provides for multiple inventory stocking sites. The INVENTORY SITES data base defines all supply (non-nursing station) inventory sites, which are defined in the STATION DRUG files. The Inventory Control Program (ICP), is used for receiving all medications from suppliers and entering the quantities received into the inventory site's supply inventory [DRUG INVENTORY QUANTITY:2]. This program is also used to remove inventory from the system for returns to the vendor, to adjust for breakage and spoilage losses, as well as the transfer of medications to alternate inventory sites.

INVENTORY TRANSFER/INVENTORY RETURNS

Inventory is transferred from the supply inventory sites to dispensing sites by means of the on-line inventory monitor program (IMON) at the request of the order entry (RXE), Medication Dispensing (MPD), Bed Change (BCH), and Print Loadsheets and Labels (PLL) programs. Once at the dispensing stations, the inventory is under control of the MPD program (which controls the dispensing of all medications). As each medication is dispensed, its station quantity count is reduced [STATION DRUG:6] a record that indicates the use of a drug is appended to the patient's journal files (PATIENT HISTORY, MEDICATION HISTORY), which are used to bill the patient. Any unused medications at the dispensing stations are returned to the station's main inventory site [STATION MASTER:14,15] by the Stock Return Program (SRP).

PRINT LOADSHEETS AND LABELS

The Print Loadsheets and Labels program is used to print the restocking load reports for each station. PLL computes the projected medication needs for each station up to the next restock, prints out the load reports in pharmacy (informing restocking personnel what quantities and types of sleeves are to be delivered to each station), and causes bulk medication order labels to be printed in pharmacy for any medications in which the station quantity is deficient to meet projected needs.

STATION LOAD REPORT

The Station Load Report (SLR) program disables the cabinet and prints out a list telling which sleeves to remove and which to install. The report lists the following:
Report title
Station name
A unique "re-enable dispenser" code (computer generated)
Date and time of report
Sleeve(s) to be removed, along with the name, quantity, form, and dosage of the medication that should be in a sleeve
Sleeve color to be inserted along with the name, quantity, form, and dosage of the medication in the sleeve

DISPENSER ROUTE FILE MAINTENANCE

The Dispenser Route File Maintenance (ROFM) program is used to maintain the dispenser reloading routes. This specifies, by route number, the days and times that each station will be reloaded. The program allows the user to:

Add a new route to the system
Change stations in an existing route
Change restock times in an existing route [DISPENSER ROUTES:4]
List entries to the screen or printer

SLEEVE EDITOR

The Sleeve Editor (EDIT) program is a powerful utility which was created so that pharmacy could have actual physical control over what drugs are in the dispenser and where they are located in the dispenser. The program allows pharmacy to:

Display what drug is in a specific sleeve [STATION SLEEVE:1]
Display what drugs are in a specific bank of sleeves [STATION SLEEVE:1]
Display what sleeves have a specified drug [STATION SLEEVE:1]
Move a sleeve to a new slot in the dispenser [STATION SLEEVE:1]
Change the current quantity of doses in any sleeve [STATION SLEEVE:2]
Change the type of sleeve currently in a dispenser slot [STATION SLEEVE:8]

RESTOCKING PROCESS

As previously mentioned, each dispensing station is assigned to a restock route and each route has one or more scheduled restocks [DISPENSER ROUTES:4] per week (preferably daily). Prior to the scheduled restocking of the dispenser, several of the restocking programs must be run which do the following:

First, the REQ program is run to determine the patient needs for the restocking period. The DISPENSER NEED file is built by REQ. The STATION DRUG file is then scanned to determine the current drug count [STATION DRUG:6[ in the dispenser. The quantity of drugs which will be used before the restock [STATION DRUG:3,5] is subtracted from the current dispenser quantity to give a projected dispenser drug count at the scheduled restock time. Each drug in the dispenser is checked for recent usage by testing the Date and Time Last Used indicator [STATION DRUG:14] in the STATION DRUG file. If the drug hasn't been used within a certain time span (based on the retention factor stored in each station's drug file [STATION DRUG:9]) then the sleeve will be scheduled to be removed. If a medication is needed which isn't currently available at the station, then the program determines if it is dispenserable [DRUG MASTER:18] and, if it is, checks to see if there is an available slot in the dispenser [STATION SLEEVE:1] (an available slot is either currently empty or contains a sleeve which is scheduled to be removed.) If there isn't an available slot, or if the drug cannot be put in the dispenser, a label is generated for the order (via the PLL program) and the patient is charged [DRUG MASTER:15] for the quantity necessary to last until the next dispenser restock. The pharmacist then sends the drug to the nursing station. The REQ program automatically chooses a slot for each drug based upon that drug's sleeve code requirements [DRUG MASTER:6] and always schedules a sleeve to be full [DRUG INVENTORY QUANTITY:4].

The LDE program may be used to override any of the REQ calculations.

Finally, the PLL program is run to print the restock load reports and to print labels for any "Bulk" medications (drugs that are needed at the dispensing station but will not be stocked in the mechanical dispenser).

Once at the station, the person restocking the dispenser logs onto the system and executes the Station Load Report (SLR). The program will produce hardcopy instructions as to which sleeves need to be removed, inserted, or changed, based upon the information generated by the REQ and LDE programs. A sleeve may be scheduled to be replaced or medications may be added to it based on options previously chosen using the LDE program. The personnel will then make all of the listed sleeve changes and close the cabinet doors. Any "Bulk" type medications are deposited in their appropriate places and then the dispenser is finally re-enabled.

To re-enable the dispenser, the following sequence is followed:

The stocking personnel logs on (again) and chooses the menu function to re-enable the dispenser. A prompt will appear on the screen for a "re-enable code" to be entered. At the top of the Station Load Report this code is printed and this code must be entered.

Upon completion of these functions, the dispenser will be re-enabled, the dispenser files will be updated to reflect any changes, and the Receive From Location fields [PATIENT ORDER:23] will be updated.

NURSING

Nurses will normally be authorized [PERSONNEL MASTER:11] for the following system functions:

Routine Meds: A "med-slip" may be printed for each RTN medication and patient selections are made. Selections may be made one at a time, as a group (per nurse), or as a group (per station). Specific patients may be selected by:

Name (phone book style) [PATIENT MASTER:2].
ID Number [PATIENT MASTER:1].
Room-Bed location [PATIENT MASTER:11].
Menu-number (per nurse-see Define Patients below).
Menu-number (per station).
For each patient selected, the program performs the following functions:
Displays the Patient Personal Profile (PPP).
Asks for patient selection verification.
Displays all routine drugs [PATIENT ORDER:18] to be administered to the selected patient this hour [PATIENT ORDER:6,10,12]. If none are scheduled, the nurse will also be informed of this fact.
If the station has a mechanical dispenser [STATION MASTER:5], the medications will be delivered to the nurse, otherwise, the nurse will be informed as to the location of the medication [PATIENT ORDER:19].

PRNs: "Med-slips" may be printed, and patients are selected and verified. All of the patient's PRN type orders (if any) are displayed and medications which are to be administered are chosen. Some PRN medications may not be available because either:

The minimum hours between doses [PATIENT ORDER:23] has not elapsed. In this case, the number of hours remaining until the next dose may be administered [PATIENT ORDER:10,23] will be displayed. Pharmacy may override this with the "stat" flag [PATIENT ORDER:27]. or:

The medication has been placed on hold [PATIENT ORDER:15]. In this case the type of the hold will be displayed [PATIENT ORDER:14]. If the station has a mechanical dispenser [STATION MASTER:5], the medication will be delivered to the nurse, otherwise, the nurse will be informed as to the location of the medication [PATIENT ORDER:19].

Pre-OPs: Again, A "med-slips" may be printed, patient choices are made (as above), and all of the patient's pre-op drugs [PATIENT ORDER:18] are displayed. Any medication which has already been drawn [PATIENT ORDER:10] will not be allowed to be dispensed again and its item number will be omitted. Any or all of the available medications may be chosen to be administered.

Bulk Re-Order: This option is selected when a patient's bulk medication needs to be re-ordered. As before, a "med-slip" may be printed, patient choices are made, and the patient's current bulk medications [PATIENT ORDER:2,18] are displayed. Choices are made by item number and, if the drug is not in the dispenser [PATIENT ORDER:19], a message will be printed in pharmacy notifying them that the drug needs to be delivered to the specified station for that patient. If the drug is in the dispenser, it will be dispensed as before (see Routine Meds).

Define Patients: As each shift begins, each nurse is encouraged to specifically define the patients who have been assigned to them for the shift [stored in PERSONNEL PATIENTS:1,2,3]. By doing so, the nurse will be able to have only those assigned patients' orders displayed during each med round. This will simplify the task of retrieving the patient's medications during that shift.

NPO Holds: This function effectively allows or probibits the release of oral medications for a specified patient [PATIENT ORDER:14,15].

Edit Patient Profile: This function allows changes to be made to a Patient's Profile. Items such as weight, age, allergies, etc. [PATIENT MASTER:4,12] may be changed.

Patient Profile List: This function prints a hardcopy of a designated patient's profile.

Patient Transfer: This function allows a patient to be transferred from one bed to another (see BED CHANGE).

Medication Inquiry: This function allows the nurse to view drug order information pertinent to the administration of a medication to a specified patient. Included in this information is the date first received [PATIENT ORDER:8], the total number of doses received [PATIENT ORDER:11], date of last renewal [PATIENT ORDER:9], and the date, time, and nurse associated with the most recent administrations. [MEDICATION HISTORY:1,3].

Patient Roster: This function prints a hardcopy of all patients at the station.

Print MAR: This function allows the nurse to selectively print Medication Administration Reports for a specific patient or all patients at the station.

Print MRR: This function allows the nurse to reprint the current Medication Round Requirements report.

Change Password: This function allows passwords to be changed [PERSONNEL Password: MASTER:5] at any time. This is useful if someone feels that their password has been compromised.

Idle This function automatically returns the system to "Idle mode" which indicates that someone else may logon to use use the system.

I claim:

1. A system for the delivery of medications under the control of a pharmacy to patients in the wards of a health care institution comprising:

a computer system;

one or more pharmacy terminals operatively connected to said computer system;

one or more dispensing stations located in the wards of said health care institution, each of said stations including,
 (a) a station terminal operatively connected to said computer system;
 (b) a station printer operatively connected to said computer system; and
 (c) a dispensing cabinet for holding a plurality of unit dose medication packages, said dispensing cabinet electrically controllable by said computer system to dispense one or more of said packages at a time;

said computer system including means for maintaining,
 (a) medication order data entered by said pharmacy, said order data indicating medication orders for patients admitted to said health care institution, said orders including the administration schedule for the medication and the identity of the dispensing station from which medications are to be obtained for said patients;
 (b) station drug data of each of said dispensing stations, said station drug data indicating the medication stored at said station and if the medication stored at said station is stored in said dispensing cabinet the location of said medications in said cabinet and the quantity of said medication currently at said dispensing station;

software means operable in said computer system for:
 (a) automatically reading said patient order data on a periodic basis and determining for each dispensing station the medication that is scheduled to be administered during an upcoming medication round to patients serviced by each said dispensing station and for generating a medication requirement report for each said determination, said report being printed at each said dispensing station on said station printer whereby it is made available to medication administration personnel; and
 (b) responding to a medication dispensing request entered at the terminal of a said dispensing station, said request for the medication ordered for a specified patient, and reading said patient order data to determine the medication scheduled to be administered to said specified patient in the upcoming medication round and:

(1) if medication scheduled to be administered in the upcoming medication round is held in the dispensing cabinet at said dispensing station at which said request is entered causing said dispensing cabinet to dispense the scheduled medication in unit dose package or packages whereby the dispensed medication may be taken by the person making the dispensing request and administered to said specified patient; and (2) if medication scheduled to be administered in the upcoming medication round is not held in the dispensing cabinet notifying the person making the request to obtain the medication from the medications stored outside the dispensing cabinet whereby the medication may be taken by the person making the request and administered to said patient.

2. A system according to claim 1 wherein said computer system further includes station stocking software means operable in said computer system for:

(a) reading said medication order data to determine the medication requirements for a specified dispensing station for a predetermined period of time, said medication order data being read to determine all orders which are to be administered from said specified dispensing station and to determine the types and quantities of medications that are scheduled to be administered from said specified dispensing station; and (b) comparing the total medication needs determined for said specified dispensing station with the quantities of medications indicated as being at said specified dispensing station by said station drug data and developing a restocking plan for said specified station which will substantially allow the needs of the patients serviced by said specified dispenstion station to be met during said predetermined period of time.

3. A system according to claim 1 wherein said medication order data includes an indication of when an ordered medication is to be discontinued and wherein said software includes means for reading said patient order data on a periodic basis to determine if any orders are to be discontinued and setting a stop indicator for said order in said patient order data if indicated, and wherein said means for automatically reading said patient order data includes means responsive to said stop indicators to prevent discontinued orders from being scheduled for administration and wherein said means for responding includes means responsive to said stop indicators so that discontinued orders will not be dispensed from said dispensing cabinet.

4. (Amended) A system according to claim 1 wherein said computer system includes means for maintaining patient data indicating demographical information about patients to be serviced by said dispensing system, and further wherein said software means includes means for displaying patient demographical data from said patient data at a said dispensing station terminal.

5. A system according to claim 1 wherein said patient order data further specifies for each said patient the room-bed assignment for said patient in said institution and a record of which room-bed assignments are supplied medications from each dispensing station and wherein said software means includes means for changing the room-bed assignment specified in said data and if the room-bed change results in said patient being moved to a room-bed assignment being serviced by a different dispensing station generating a report and causing said report to be printed at said patient's previous dispensing station, said report informing transferring personnel to retrieve any of said patient's medications not held in said dispensing cabinet and to transfer them along with the patient to the new room-bed assignment.

6. (New) A system according to claim 5 wherein said computer system includes means for reserving medications at said dispensing stations according to the medication orders specified in said medication order data and further including software means for cancelling the reservations at said previous dispensing station attributable to said patient being reassigned and reserving the medications attributable to said patient at said different dispensing station.

7. A system according to claim 1 including means for monitoring various status conditions of the dispensing cabinets, said status conditions including access doors being open/closed, dispenser being active/idle, dispenser being enabled/disabled, dispenser elevator being up/down, polling being enabled/disabled, and power failure status, said status conditions being monitored to determine aspects of said dispensing cabinet's operations including whether or not said dispensing cabinet is online, whether or not to allow medications to be accessed from said dispensing cabinet, and whether or not said dispenser has experienced a power failure said means for monitoring further including means for causing a report to be generated at said pharmacy terminal notifying pharmacy personnel of a sensed operation problem.

8. A system according to claim 1 including means for sensing operatioal problems associated with said dispensing stations, said operational problems including loss of power to the dispenser, communication line failures, and interface failure, and means for attempting to automatically rectify a sensed operational problem and if said problem cannot be rectified printing a notice of said problem on said station printer.

9. A system according to claim 1 further wherein said computer system includes means for maintaining drug master data specifying medications available to the pharmacy of said health care institution, said drug master data specifying interaction information and therapeutic equivalent information for each said medication, and further wherein said means for maintaining said medication order data includes software means operable on said computer for enabling a new medication order to be entered into said medication order data from a said pharmacy terminal, and for reading said drug master data and said medication data order to determine if a said new medication order is therapeutically equivalent to any prior medication orders entered for the same patient and for determining if said medication order has an interaction problem with another drug order for the same patient, and for warning the personnel entering said new medication order of any interaction problem or therapeutic equivalent medication identified, said warning issued on said pharmacy terminal.

10. A new system according to claim 1 further including software means for enabling new medication orders to be entered at said pharmacy terminal.

11. (Amended) A system according to claim 10 wherein said software means includes means for notifying said pharmacy personnel of medications that are ordered for a specified patient that are not stored at said dispensing station servicing said specified patient so that said ordered medication can be delivered to said station from another location.

12. A system according to claim 10 further wherein said computer system includes means for maintaining patient data indicating any allergies any of said patients have and further software means responsive to the entry of a new order in said medication order data for checking to see whether the ordered medication would cause an allergic reaction for said patient for which the order is entered based on said allergy indications in said patient data.

13. A system according to claim 10 further wherein said medication order data includes data specifying a message related to a particular medication ordered to be administered, and further wherein said software means includes means for displaying a said specified message for a medication dispensed from a said station, said message being displayed on said station terminal.

14. A system according to claim 10 further wherein said software means includes means for notifying pharmacy personnel entering a new order of the quantity of the medication ordered available in the station supplying the patient, said notification generated on said pharmacy terminal.

15. A system according to claim 1 wherein said means for maintaining includes means for specifying said orders to be placed on hold, and further wherein said dispensing control means includes means for preventing orders which are specified as being on hold from being dispensed from said dispensing cabinet.

16. A system according to claim 1 further wherein said means for maintaining reduces the quantity specified for a particular medication in said station drug data each time said particular medication is dispensed from said dispensing cabinet.

17. A system according to claim 1 further wherein said means for maintaining reduces the quantity specified for a particular medication in said station drug data each time a notice to dispense said particular medication is issued.

18. A system according to claim 1 further including software means for recording medications dispensed to said patients.

19. A system according to claim 18 further wherein said medication requirement report specifies medications previously scheduled to be dispensed but which were not dispensed so that medication administration personnel are notified of scheduled orders which were not administered at the specified scheduled time.

20. A system according to claim 1 wherein said medication order drug data includes an indication of when an ordered medication is to be discontinued and wherein said software means includes means for reading said patient order data on a periodic basis to determine if any orders are to be discontinued within an upcoming pedetermined time period and for causing a medication discontinue notice report to be printed at each said station on said station printer, said report indicating which medications are to be discontinued within said predetermined period.

21. A system according to claim 1 wherein said cabinet includes as a means for preventing the medications held in said dispensing cabinet from being accessed by medication administration personnel until dispensed from said cabinet.

22. A system for dispensing medications in unit dose packages to patients in a health care institution, comprising:

one or more dispensing cabinet means for holding a plurality of different types of said medications in unit dose packages, and each selectively controllable for dispensing any one of said different types of medications one or more of said unit dose packages at a time;

a dispensing cabinet printer means for each said dispensing cabinet means;

control means connected for controlling said dispensing cabinet means and said printer means, said control means including;

(a) database means for holding medication order data specifying medication orders for patients in said institution in accordance with medication prescriptions for said patients, each said order specifying the medication dose, the scheduled times for administration of said dose and which of said dispensing cabinet means it is to be dispensed from;

(b) dispensing control means responsive to said medication order data for controlling each said dispensing cabinet means to cause each to selectively dispense for a said patent a said dose in accordance with said medication order data, said dispensing control means capable of causing any one of said unit dose packages of any of said different types of medications to be dispensed for any one of said patients; and (c) report generating means responsive to said data for preparing a medication requirement report for each of said dispensing cabinet means and for causing said report to be printed at said dispensing cabinet printer means for each said dispensing cabinet means, said medication requirement report having information on the doses being dispensed for each said patient, including the scheduled time for administration of said dose, whereby doses dispensed from said dispensing cabinet means can be taken and administered to said patients in accordance with said medication requirement report.

23. A system according to claim 22 wherein said control means further includes terminal means for inputting control commands to said control means and for inputting new medication orders into said database means.

24. A system according to claim 23 wherein said medication order data includes means for designating one of said medication orders to be placed on hold, and further wherein said dispensing control means includes means for preventing orders which are specified as being on hold from being dispensed from said dispensing cabinet means, said designation entered at said terminal means.

25. A system according to claim 23 including further database means for holding medication interaction data specifying the interaction characteristics of said medications, and further wherein said control means includes means for warning pharmacy personnel inputting new medication orders if said medication specified in said new order has a interaction characteristic which would cause it to interact with a medication previously ordered for said patient.

26. A system according to claim 22 further wherein said medication order data includes data specifying a message related to a particular medication ordered to be administered, and further wherein said control means includes means for displaying said message at said dispensing cabinet means when said medication dose is dispensed.

27. A system according to claim 22 further wherein said patient medication order data includes an indication of when an ordered medication is to be discontinued and wherein said control means includes means for reading said medication order data on a periodic basis to determine if any orders are to be discontinued within an upcoming predetermined time period and for causing a medication discontinue notice report to be printed on said dispensing cabinet printer means, said report indicating which medications are to be discontinued within said predetermined period.

28. A system according to claim 22 further wherein said medication requirement report specifies medications previously scheduled to be dispensed but which were not dispensed so that medication administration personnel are notified of scheduled orders which were not administered at the specified scheduled time.

29. A system according to claim 22 further wherein said control means includes means responsive to the specified scheduled times in said data for administration of a said dose to cause each said dose to be dispensed from said cabinet means at times corresponding to said specified scheduled times whereby the release of said doses from said dispensing cabinet means is substantially in accordance with the administration schedule for said dose.

30. A system according to claim 22 further wherein medications are dispensed to said patients in periodic rounds and further wherein said report generating means includes means for causing said medication requirement report to be printed periodically in accordance with the timing of said medication rounds for said patients.

31. A system according to claim 30 further wherein said report generating means includes means responsive to said data for preparing a medication administration report for at least said patients for which medication doses are ordered as specified in said medication order data and for causing said report to be printed at said dispensing cabinet printer means, said medication administration report having information on all the ordered doses scheduled to be dispensed for each of said patients during an upcoming predetermined time period encompassing a plurality of said medication rounds, whereby said medication administration report can be used as a permanent record of the administration of doses to said patients.

32. A system according to claim 22 wherein said report generating means further includes means for causing said medication requirement report for said patients to be printed before said doses are dispensed from said cabinet means.

33. A system for dispensing medications in a health care institution, comprising:
  one or more dispensing stocks for holding a plurality of different types of said medications;
  a dispensing stock printer means for each said dispensing stock;
  control means connected for controlling said dispensing stock printer means, said control means including:
    (a) database means for holding medication order data specifying medication orders for patients in said institution in accordance with medication prescriptions for said patients, each said order specifying the medication dose, the scheduled times for administration of said dose and which of said dispensing stocks it is to be administered from; and
    (b) report generating means responsive to said data for preparing a medication requirement report for each of said dispensing stocks and for causing said report to be printed at said dispensing stock printer means for each said dispensing stock, said medication requirement report having information on the dose to be administered for each said patient, including the scheduled time for administration of said dose, whereby doses can be taken from said stock and administered to said patients in accordance with said medication requirement report.

34. A system according to claim 33 wherein said control means further includes terminal means for inputting control commands to said control means and for inputting new medication orders into said database means.

35. A system according to claim 34 wherein said medication order data includes means for designating one of said medication orders to be placed on hold, and further wherein said control means includes means for preventing orders which are specified as being on hold from being specified in said administration requirement report as to be administered, said designation entered at said terminal means.

36. A system according to claim 34 including further database means for holding medication interaction data specifying the interaction characteristics of said medications, and further wherein said control means includes means for warning pharmacy personnel inputting new medication orders if said medication specified in said new order has a interaction characteristic which would cause it to interact with a medication previously ordered for said patient.

37. A system according to claim 33 further wherein said medication order data includes data specifying a message related to a particular medication ordered to be administered, and further wherein said control means includes means for displaying said message at said dispensing stock when said medication dose is specified to be administered.

38. A system according to claim 33 further wherein said patient medication order data includes an indication of when an ordered medication is to be discontinued and wherein said control means includes means for reading said medication order data on a periodic basis to determine if any orders are to be discontinued within an upcoming predetermined time period and for causing a medication discontinue notice report to be printed on said dispensing stock printer means, said report indicating which medications are to be discontinued within said predetermined period.

39. A system according to claim 33 further wherein medications are dispensed to said patients in periodic rounds and further wherein said report generating means includes means for causing said medication requirement report to be printed periodically in accordance with the timing of said medication for said patients.

40. A system according to claim 39 further wherein said report generating means includes means responsive to said data for preparing a medication administration report for at least said patients for which medication doses are ordered as specified in said medication order data and for causing said report to be printed at said dispensing stock printer means, said medication administration report having information on all the ordered doses scheduled to be administered for each of said patients during an upcoming predetermined time period encompassing a plurality of said medication rounds, whereby said medication administration report can be used as a permanent record of the administration doses to said patients.

41. A system according to claim 33 further wherein said medication requirement report specifies medications previously scheduled to be dispensed but which were not dispensed so that medication and administration personnel are notified of scheduled orders which were not administered at the specified scheduled time.

42. A system for dispensing medications in unit dose packages to patients in a health care institution, comprising:
one or more dispensing cabinet means for holding a plurality of different types of said medications in unit dose packages, and each selectively controllable for dispensing any one of said different types of medications one or more of said unit dose packages at a time;
a dispensing cabinet printer means for each of said dispensing cabinet means;
control means connected for controlling said dispensing cabinet means and said printer means, said control means including:
(a) database means for holding medication order data specifying medication orders for patients in said institution in accordance with medication prescriptions for said patients, each said order specifying the medication dose, the scheduled times for administration of said medication dose and which of said dispensing cabinet means it is to be dispensed from;
(b) dispensing control means including a dispensing cabinet input means for each said dispensing cabinet means so that each said dispensing cabinet means has an associated input means, said input means for entering a request to dispense medication for a specified patient from its associated dispensing cabinet means, said control means responsive to a said request for controlling a said dispensing cabinet means to cause it to selectively dispense for said specified patient each said dose ordered to be administered to said specified patient according to said orders, each said dose being dispensed from said cabinet means in said unit dose packages, said dispensing control means capable of causing any one of said unit dose packages of any of said different types of medications to be dispensed for any one of said patients; and
(c) report generating means responsive to said data for preparing a medication requirement report for each of said dispensing cabinet means and for causing said medicatio requirement report to be printed on said printer means for each said dispensing cabinet means, said medication requirement report having information on each said dose dispensed for said patients, including the dose and scheduled time for administration, whereby said doses dispensed from said dispensing cabinet means can be taken and administered to said patients in accordance with said medication requirement report.

43. A system according to claim 42 wherein said control means further includes terminal means for inputting control commands to said control means and for inputting new medication orders into said database means.

44. A system according to claim 43 wherein said medication order data includes means for designating one of said medication orders to be placed on hold, and further wherein said control means includes means for preventing orders which are specified as being on hold from being dispensed from said dispensing cabinet means, said designation entered at said terminal means.

45. A system according to claim 43 including further database means for holding medication interaction data specifying the interaction characteristics of said medications, and further wherein said control means includes means for warning pharmacy personnel inputting a new medication order if said medication specified in said new order has an interaction characteristic which would cause it to interact with a medication previously ordered for said patient.

46. A system according to claim 42 further wherein said medication order data includes data specifying a message related to a particular medication ordered to be administered, and further wherein said control means includes means for displaying said message at said dispensing cabinet means when said medication dose is dispensed.

47. A system according to claim 42 further wherein said medication order data includes an indication of when an ordered medication is to be discontinued and wherein said control means includes means for reading said medication order data on a periodic basis to determine if any orders are to be discontinued within an upcoming predetermined time period and for causing a medication discontinue notice report to be printed on said dispensing cabinet printer means, said report indicating which medications are to be discontinued within said predetermined period.

48. A system according to claim 42 further wherein said medication requirement report specifies medications previously scheduled to be dispensed but which were not dispensed so that medication and administration personnel are notified of scheduled orders which were not administered at the specified scheduled time.

49. A system according to claim 42 wherein said dispensing control means includes means for determining from said medication order data whether a said dose for said specified patient is scheduled to be administered within a predetermined time from the time said request is entered and causing said dispensing cabinet means to dispense only each said dose scheduled to be administered within said predetermined time period.

50. A system according to claim 42 further wherein for each said dose ordered to be administered as-needed said scheduled times in said data specify a predetermined quantity of dose to be administered no more often than a predetermined number of hours, and further wherein said dispensing control means includes timing means responsive to a said request for preventing said as-needed ordered medication from being dispensed from said dispenser cabinet means at the time of said request if said predetermined quantity of doses have been dispensed within said predetermined number of hours.

51. A system according to claim 50 further wherein for said as-needed ordered medications said data specifies a maximum number of doses to be administered during a predetermined block of time and further wherein said timing means includes means for preventing more than said maximum number of doses to be dispensed during said block of time.

52. A system according to claim 42 further wherein said medications are dispensed to said patients in periodic rounds and further wherein said report generating means includes means for causing said medication requirement report to be printed periodically in accordance with the timing of said medication rounds for said patients.

53. A system according to claim 52 further wherein said report generating means includes means responsive to said data for preparing a medication administration report for at least said patients for which a said dose is ordered as specified in said order data and for causing said report to be printed at said printer means, said medication administration report having information on all the ordered doses scheduled to be dispensed for said patients during an upcoming predetermined time period encompassing a plurality of medication rounds, whereby said medication administration report can be used as a permanent record of the administration of doses to said patients.

54. A system according to claim 42 wherein said report generating means further includes means for causing said medication requirement report for said patients to be printed before a said dose is dispensed from said cabinet means.

55. A system for dispensing medications to patients in a health care institution, comprising:
one or more dispensing stocks for holding a plurality of different types of said medications;
a dispensing stock printer means and a dispensing stock terminal for each of said dispensing stocks;
control means connected for controlling said dispensing stock terminal and said printer means, said control means including:
(a) database means for holding medication order data specifying medication orders for patients in said institution in accordance with medication prescriptions for said patients, each said order specifying the medication dose, the scheduled times for administration of said medication dose and which of said dispensing stocks it is to be dispensed from;
(b) dispensing control means including input means for entering a request to specify medication to be administered for a specified patient, said control means responsive to a said request for causing said dispensing stock terminal to identify for said specified patient each said dose ordered to be administered to said specified patient according to said orders and the location of each said dose in said stock whereby said dose can be taken from said stock; and
(c) report generating means responsive to said data for preparing a medication requirement report for each of said dispensing stocks and for causing said medication requirement report to be printed on said printer means for each dispensing stock, said medication requirement report having information on each said dose to be administered to said patients, including the dose and scheduled time for administration, whereby said medication administration personnel can request said control means to specify the location of said dose so that it can be taken and administered to said patients in accordance with said medication requirement report.

56. A system according to claim 55 wherein said control means further includes pharmacy terminal means for inputting control commands to said control means and for inputting new medication orders into said database means.

57. A system according to claim 56 wherein said medication order data includes means for designating one of said medication orders to be placed on hold, and further wherein said control means includes means for preventing orders which are specified as being on hold from being specified as to be administered at said dispensing stock terminal, said designation entered at said pharmacy terminal means.

58. A system according to claim 56 including further database means for holding medication interaction data specifying the interaction characteristics of said medications, and further wherein said control means includes means for warning pharmacy personnel inputting a new medication order if said medication specified in said new order has an interaction characteristic which would cause it to interact with a medication previously ordered for said patient.

59. A system according to claim 55 further wherein said medication order data includes data specifying a message related to a particular medication ordered to be administered, and further wherein said control means includes means for displaying said message at said stock terminal.

60. A system according to claim 55 further wherein said patient medication order data includes an indication of when an ordered medication is to be discontinued and wherein said control means includes means for reading said medication order data on a periodic basis to determine if any orders are to be discontinued wihin an upcoming predetermined time period and for causing a medication discontinue notice report indicating which medications are to be discontinued within said predetermined period.

61. A system according to claim 55 further wherein said medication requirement report specified medications previously scheduled to be dispensed but which were not specified in response to a request at said dispensing stock terminal so that medication and administration personnel are notified of scheduled orders which were not administered at the specified scheduled time.

62. A system according to claim 55 wherein said dispensing control means includes means for determining from said medication order data whether a said dose for said specified patient is scheduled to be administered within a predetermined time from the time said request is entered and causing said dispensing stock terminal to specify for administration only each said dose scheduled to be administered within said predetermined time period.

63. A system according to claim 55 further wherein for each said dose ordered to be administered as-needed said scheduled times in said data specify a predetermined quantity of dose to be administered no more often than a predetermined number of hours, and further wherein said dispensing control means includes timing means responsive to a said request for preventing said as-needed ordered medication from being specified for administration at the time of said request within said predetermined number of hours.

64. A system according to claim 63 further wherein for said as-needed ordered medications said data specifies a maximum number of doses to be administered during a predetermined block of time and further wherein said timing means includes means for preventing more than said maximum number of doses to be specified for administration during said block of time.

65. A system according to claim 55 further wherein said medications are dispensed to said patients in periodic rounds and further wherein said report generating means includes means for causing said medication requirement report to be printed periodically in accordance with the timing of said medication rounds for said patients.

66. A system according to claim 65 further wherein said report generating means includes means responsive to said date for preparing a medication administration report for at least said patients for which a said dose is ordered as specified in said order data and for causing said report to be printed at said printer means, said medication administration report having information on all the ordered doses scheduled to be administered for said patients during an upcoming predetermined time period encompassing a plurality of medication rounds, whereby said medication administration report can be used as a permanent record of the administration of doses to said patients.

67. A system according to claim 55 wherein said report generating means further includes means for causing said medication requirement report for said patients to be printed before a said dose is specified to be dispensed.

68. A system for delivering medications to patients in a health care institution, said institution having a pharmacy supply stock of medications, said system comprising:
one or more dispensing cabinet means for holding a plurality of different types of said medications in unit dose packages, and each selectively controllable for dispensing any one of said different types of medications one or more of said unit dose packages at a time, said medications stocked in said cabinet means from said pharmacy supply stock;
control means connected for controlling said dispensing cabinet means, said control means including:
(a) first database means for holding medication order data specifying medication orders for patients in said institution in accordance with medication prescriptions for said patients, each said order specifying the medication dose, the scheduled times for administration of said dose and which of said dispensing cabinet means it is to be dispensed from;
(b) second database means for holding dispensing cabinet medication data specifying the types, quantity and location of unit dose packages held in each of said dispensing cabinet means;
(c) dispensing control means responsive to said medication order data for controlling each said dispensing cabinet means to cause each to selectively dispense for said patient a said dose in accordance with said orders, said dose being dispensed from said cabinet means in said unit dose packages, said dispensing control means capable of causing any one of said unit dose packages of any of said different types of medications to be dispensed for any one of said patients;
(d) pharmacy terminal means for inputting new medication order data so that new medication orders can be specified in said medication order data, and for outputting notifications; and
(e) allocation means for reserving unit dose packages held in each said cabinet means according to medication orders specified in said medication order data, said allocation means including means for determining for each new medication order specified whether a said dispensing cabinet means is currently holding unreserved unit dose packages which can be reserved to fulfill said new medication order and if an insufficient quantity is available notifying institution personnel on said pharmacy terminal means so that medications to fulfill the order can be delivered to said patient from said supply stock.

69. A system according to claim 68 wherein said medication order data includes means for designating one of said medication orders to be placed on hold, and further wherein said dispensing control means includes means for preventing orders which are specified as being on hold from being dispensed from said dispensing cabinet means, said designation entered at said pharmacy terminal means.

70. A system according to claim 68 further including further database means for holding medication interaction data specifying the interaction characteristics of said medications, and further wherein said control means includes means for warning pharmacy personnel inputting new medication orders at said terminal means if said medication specified in said new order has a interaction characteristic which would cause it to interact with a medication previously ordered for said patient.

71. A system according to claim 68 further wherein said medication order data includes data specifying a message related to a particular medication ordered to be administered, and further wherein said control means includes means for displaying said message at a said dispensing cabinet means when said medication dose is dispensed.

72. A system according to claim 68 wherein said patient medication order data includes an indication of when an ordered medication is to be discontinued and wherein said control means includes printer means and means for reading said medication order data on a periodic basis to determine if any orders are to be discontinued within an upcoming predetermined time period and for causing a medication discontinue notice report to be printed on said printer means, said report indicating which medications are to be discontinued within said predetermined period.

73. A system according to claim 68 further wherein said second database means includes a restocking schedule for each said dispensing cabinet means and further wherein said allocation means includes means for determining the quantity of unit dose packages that have to be delivered from said supply stock to fulfill a medication order until the next scheduled restocking of said cabinet means.

74. A system according to claim 73 further including database means for maintaining inventory data specifying the type and quantity of medications held in said pharmacy supply stock and further including means for reducing the quantity of medication specified therein each time medications are transferred from said supply stock to said cabinet means.

75. A system according to claim 68 further wherein said second database means includes a restocking schedule for each said dispensing cabinet means and further wherein said control means includes means for determining a restocking plan for said dispensing cabinet means, said restocking plan for said dispensing cabinet means, said restocking plan determined according to the quantity of doses ordered to be administered to said patients as specified in said medication order data and according to the quantity and type of medication doses in said dispensing cabinet means as determined from said dispensing cabinet means as determined from said dispensing cabinet medication data, and further wherein said system includes printing means for printing said restocking report whereby pharmacy personnel can assemble necessary unit dose packages to be stocked in said dispensing cabinet means.

76. A system for dispensing medications to patients in a health care institution, said institution having a pharmacy supply stock, said system comprising:

one or more station dispensing stocks of a plurality of different types of said medications, said medications stocked in said dispensing stocks from said pharmacy supply stock, said dispensing stocks used to fulfill the medication needs of said patients:

control means for controlling the dispensing of said medications including:

(a) first database means for holding medication order data specifying medication orders for patients in said institution in accordance with medication prescriptions for said patients, each said order specifying the medication dose, the scheduled times for administration of said dose and which of said dispensing stocks it is to be administered from;

(b) second database means for holding dispensing stock medication data specifying the types and quantities of medications stocked in each of said dispensing stocks;

(c) a station terminal connected to said control means;

(d) station notification means responsive to said medication orders for generating a report to notify medication administration personnel of each said medication dose ordered to be administered to said patients as specified in said medication order data, said report generated at said station terminal means;

(e) pharmacy terminal means for inputting new medication order data so that new medications ordered to be administered can be specified in said medication order data, and for outputting notifications; and (f) allocation means for reserving medications stocked in each said dispensing stock according to medication orders specified in said medication order data, said allocation means including means for determining for each new medication order specified whether a said dispensing stock is currently stocked with unreserved medications which can be reserved to fulfill said new medication order and, if an insufficient supply is available in said dispensing stock notifying institution personnel on said pharmacy terminal means so that medications to fulfill the order can be delivered to said patient from said pharmacy supply stock.

77. A system according to claim 76 wherein said medication order data includes means for designating one of said medication orders to be placed on hold, and further wherein said dispensing control means includes means for preventing said administration personnel from being notified to administer a medication which is ordered under an order which is specified as being on hold, said designation entered at said pharmacy terminal means.

78. A system according to claim 76 including further database means for holding medication interaction data specifying the interaction characteristics of said medications, and further wherein said control means includes means for warning pharmacy personnel inputting new medication orders on said pharmacy terminal if said medication specified in said new order has a interaction characteristic which would cause it to interact with a medication previously ordered for said patient.

79. A system according to claim 76 further wherein said medication order data includes data specifying a message related to a particular medication ordered to be administered, and further wherein said control means includes means for displaying said message to said administration personnel on said station terminal when said notification to administer said medication is generated.

80. A system according to claim 76 wherein said patient medication order data includes an indication of when an ordered medication is to discontinue and wherein said control means includes printer means and means for reading said medication order data on a periodic basis to determine if any orders are to be discontinued within an upcoming predetermined time period and for causing a medication discontinue notice report to be printed on said printer means, said report indicating which medications are to be discontinued within said predetermined period.

81. A system according to claim 76 further wherein said second database means includes a restocking schedule for each said dispensing stock and further wherein said allocation means includes means for determining the supply of medications that has to be delivered to fulfill a medication order until the next scheduled restocking of said dispensing stock.

82. A system according to claim 76 further wherein said second database means includes a restocking schedule for each said dispensing stock and further wherein said control means includes means for determining a restocking plan for each said dispensing stock, said restocking plan determined according to the medications ordered to be administered to said patients as specified in said medication order data and according to the type and quantity of medications in each said dispensing stock as determined from said dispensing stock medication data, and further wherein said system includes printing means for printing said restocking plan whereby pharmacy personnel can assemble necessary medications to be delivered to said dispensing stock.

83. A system according to claim 76 further including dispensing cabinet means for holding a plurality of different types of said medications in unit dose packages, and selectively controllable by said dispensing control means for dispensing any one of said different types of medications one or more of said unit dose packages at a time, said medications stocked in said cabinet means from said pharmacy supply stock, said dispensing control means including means responsive to said medication order data for controlling said dispensing cabinet means to cause it to selectively dispense unit dose packages of said medications as specified in said medication order data.

84. A system according to claim 76 wherein said dispensing stock is a floor stock.

85. A system according to claim 76 wherein said dispensing stock is held in a cart delivered from said pharmacy supply stock.

86. A system for delivering medications to patients in two or more wards of a health care institution, said institution having a pharmacy supply stock of said medications, said system comprising:
- a dispensing stock of different types of said medications located in a first of one of said wards, said medications stocked in said dispensing stock from said pharmacy supply stock;
- dispensing cabinet means for holding a plurality of different types of said medications in unit dose packages, and selectively controllable for dispensing any one of said different types of medications one or more of said unit dose packages at a time, said medications stocked in said cabinet means from said pharmacy supply stock, said dispensing cabinet means located in a second one of said wards;
- control means for controlling the delivery of said medications including:
  - (a) database means for holding medication order data specifying medication orders for patients in said institution in accordance with medication prescriptions for said patients, said orders specifying the dose and the scheduled times for administration of said dose, and which wards the patients are located in;
  - (b) second database means for holding medication stock data specifying the types and quantities of medications held in said dispensing stock and the types, quantities and locations of medication unit dose packages held in said dispensing cabinet means;
  - (c) pharmacy terminal means for inputting new medication order data so that new medications ordered to be administered can be specified in said medication order data, and for outputting notifications;
  - (d) dispensing control means responsive to said medication order data for controlling said dispensing cabinet means to cause it to selectively dispense for a said patient a said dose in accordance with said orders, said dose being dispensed from said cabinet means in said unit dose packages said dispensing control means capable of causing any one of said unit dose packages of any of said different types of medications to be dispensed for any one of said patients;
  - (e) a station terminal connected to said control means;
  - (f) notification means responsive to said medication order data for generating a report at said station terminal for notifying the personnel in said first one of said wards of medications ordered to be administered from said dispensing stock to said patients in said first one of said wards; and
  - (g) allocation means for reserving medications held in said cabinet means and in said dispensing stock according to medications orders specified in said medication order data, said allocation means including means for determining for each new medication order specified whether the specified medication order can be filled from unreserved medications and if an insufficient supply is available notifying institution personnel on said pharmacy terminal means so that medications to fill the order can be delivered to said patient from said pharmacy supply stock.

87. A system according to claim 86 further wherein said second database means includes a restocking schedule for said dispensing stock and said dispensing cabinet means stock and further wherein said allocation means includes means for determining the supply of medications that has to be delivered to fulfill a medication order until the next scheduled restocking of said cabinet means and said dispensing stock.

88. A system according to claim 86 further wherein said second database means includes a restocking schedule for said cabinet means and said dispensing stock and further wherein said control means includes means for determining a restocking plan for each said dispensing stock and said cabinet means, said restocking plan determined according to the medications ordered to be administered to said patients as specified in said medication order data and according to the medications held in said dispensing stock and said cabinet means, and further wherein said system includes printing means for printing said restocking plan whereby pharmacy personnel can assemble necessary medications to be delivered to each said dispensing stock and said cabinet means.

89. A system according to claim 86 wherein said dispensing stock is a floor stock.

90. A system according to claim 86 wherein said dispensing stock is held in a cart delivered from said pharmacy supply stock.

91. A system for delivering medications to patients in a health care institution, said system comprising;
- a stock of plurality of different types of said medications, used to fulfill the medication needs of said patients;
- control means for controlling the delivery of said medications including:
  - (a) first database means for holding medication order data specifying medication orders for patients in said institution in accordance with medication prescriptions for said patients, said orders specifying the dose and the scheduled times for administration of said doses;
  - (b) second database means for holding drug master data specifying medications available to the pharmacy of said health care institution, said drug master data specifying interaction information and therapeutic equivalent information for each said medication;
  - (c) terminal means for entering a new medication order into said medication order data; and
  - (d) means for reading said drug master data and said medication data order to determine if a said new medication order is therapeutically equivalent to any prior medication orders for the same patient and for determining if a said new medication order has an interaction problem with other medication order for the same patient, and for warning the personnel entering said new medication order of any interaction problem or therapeutic equivalent medication identified, said warning issued on said terminal means;
  - (e) a station terminal connected to said control means; and
  - (f) notification means for generating a report to notify medication administration personnel of each said medication dose ordered to be administered to said patients as specified in said medication order data, said report generated at said station terminal.

92. A system according to claim 91 further including cabinet means for holding said station stock, said cabinet means controllable by said control means to selectively dispense said medications in accordance with said orders.

93. A system according to claim 91 wherein said drug master data includes data specifying a message related to a particular medication represented by said data, and further wherein said dispensing control means includes means for displaying a said specified message on said pharmacy terminal means when an order for medication is entered.

94. A system according to claims 22, 42, or 68 wherein said patients are located in one or more wards of said institution and further wherein said dispensing cabinet means are located in said wards.

95. A system according to claims 33, 55, or 76 wherein said patients are located in one or more wards of said institution and further wherein said dispensing stocks are located in said wards.

96. A system according to claims 22, 42, or 68 wherein said cabinet means includes door means for preventing the medications held in said cabinet means from being accessed by medication administration personnel until dispensed from said cabinet means.

97. A system for creating a schedule for the administration of routine medications comprising:

(a) computer means including storage means, display means and input means;
(b) data stored in said storage means specifying a plurality of standard medication schedules, said data including an entry for each different schedule specified, each of said entries including an alphanumeric descriptor of said schedule and a specification of the corresponding daily hours schedule for administration;
(c) software means operable on said computer means for displaying a '24 hour clock on said display means, said clock including an individual representation for each hour in the day; said software means including:
(d) means responsive to said input means so that one of said schedules can be selected from said data;
(e) means for displaying scheduled hours indicators adjacent said displayed 24 hour clock which indicate which hours are scheduled for medication administration according to the selected schedule from said data;
(f) means responsive to said input means for adding new scheduled hour indicators or deleting scheduled hour indicators adjacent said individual representations for each hour in the day until the desired indicated scheduled hours are obtained; and
(g) means for creating a medication administration schedule in accordance with the scheduled hour indicators displayed on said display means, said administration schedule of a medication ordered for a patient.

* * * * *

UNITED STATES PATENT AND TRADEMARK OFFICE
CERTIFICATE OF CORRECTION

PATENT NO. : 4,847,764

DATED : July 11, 1989

INVENTOR(S) : Jerry L. Halvorson

It is certified that error appears in the above-identified patent and that said Letters Patent is hereby corrected as shown below:

In Col. 1, the paragraph beginning on line 11 should be inserted before "Technical Field of the Invention".

Col. 2, line 13, "7≥8" should be --7-8--.

Col. 2, line 26, after "the", insert --applicant's invention;--.

Col. 2, line 60, after "ability" insert --to--.

Col. 2, line 68, "centeral" should be --central--.

Col. 3, line 30, "30" should be --20--.

Col. 3, line 51, "catagorized" should be --categorized--.

Col. 4, line 34, "catagories" should be --categories--.

Col. 5, line 16, "from" should be --for--.

Col. 5, line 45, "medications" should be --Medications--.

Col. 7, line 13, "accomodate" should be --accommodate--.

Col. 7, line 18, after "in" insert --the--.

Col. 9, line 45, "numbr" should be --number--.

Col. 10, line 44, delete "91".

Col. 10, line 47, after "file" insert --91--.

Col. 11, line 39, "The" should begin a new line.

UNITED STATES PATENT AND TRADEMARK OFFICE
CERTIFICATE OF CORRECTION

PATENT NO. : 4,847,764

DATED : July 11, 1989

INVENTOR(S) : Jerry L. Halvorson

It is certified that error appears in the above-identified patent and that said Letters Patent is hereby corrected as shown below:

Col. 14, line 13, "8" should be --18--.

Col. 14, line 31, "ORDERS" should be --ORDER--.

Col. 15, line 2, "1 & 3" should be --1 & 2--.

Col. 15, line 17, "a" should be --an--.

Col. 15, line 41, "1" should be --4--.

Col. 16, line 7, "needeed" should be --needed--.

Col. 16, line 66, "interactons" should be --interactions--.

Col. 17, line 45, after "is" in the first instance, insert --required--.

Col. 19, line 18, "Determine" should be --Determines--.

Col. 19, line 26, after "determined" insert --time--.

Col. 21, line 41, "6[" should be --6]--.

Col. 24, line 9, delete "Password:".

Col. 24, line 12, "Idle" should be --Idle:--.

Col. 24, line 14, "logon" should be --log on--.

Col. 24, lines 34-35, "maintianing" should be --maintaining--.

Col. 24, line 47, insert a comma after "cabinet".

UNITED STATES PATENT AND TRADEMARK OFFICE
CERTIFICATE OF CORRECTION

PATENT NO. : 4,847,764

DATED : July 11, 1989

INVENTOR(S) : Jerry L. Halvorson

It is certified that error appears in the above-identified patent and that said Letters Patent is hereby corrected as shown below:

Col. 25, line 37, "dispenstion" should be --dispensing--.

Col. 25, line 54, delete "(Amended)".

Col. 26, line 8, delete "(New)".

Col. 26, line 34, "operatioal" should be --operational--.

Col. 26, line 64, delete "(Amended)".

Col. 27, line 56, "pedetermined" should be --predetermined--.

Col. 31, line 59, "medicatio" should be --medication--.

Col. 35, line 15, "date" should be --data--.

Col. 40, line 59, "other" should be --another--.

Col. 42, line 13, "said" should begin a new line.

Signed and Sealed this

Twenty-fifth Day of December, 1990

Attest:

HARRY F. MANBECK, JR.

Attesting Officer

Commissioner of Patents and Trademarks

(12) REEXAMINATION CERTIFICATE (4437th)
United States Patent
Halvorson

(10) Number: US 4,847,764 C1
(45) Certificate Issued: Sep. 11, 2001

(54) SYSTEM FOR DISPENSING DRUGS IN HEALTH CARE INSTITUTIONS

(75) Inventor: Jerry L. Halvorson, Rapid City, SD (US)

(73) Assignee: Meditrol Inc., Rapid City, SD (US)

Reexamination Request:
No. 90/004,344, Aug. 28, 1996

Reexamination Certificate for:
Patent No.: 4,847,764
Issued: Jul. 11, 1989
Appl. No.: 07/053,067
Filed: May 21, 1987

Certificate of Correction issued Dec. 25, 1990.

(51) Int. Cl.[7] .................................................. G06F 19/00
(52) U.S. Cl. ........................ 700/231; 700/232; 700/236; 700/241; 700/243; 340/309.4; 221/2
(58) Field of Search ........................ 700/230, 232, 700/233, 236, 237, 241, 242, 243, 213, 216

(56) References Cited

U.S. PATENT DOCUMENTS

| | | | |
|---|---|---|---|
| 3,762,601 | 10/1973 | McLaughlin | 221/2 |
| 4,655,026 | 4/1987 | Wigoda | 53/55 |
| 4,695,954 | 9/1987 | Rose et al. | 364/413 |
| 4,733,362 | 3/1988 | Haraguchi | 364/479 |
| 4,831,562 * | 5/1989 | McIntosh et al. | 364/569 |
| 4,953,745 * | 9/1990 | Rowlett, Jr. | 221/5 |

OTHER PUBLICATIONS

"American Journal of Hospital Pharmacy" magazine, Jun. 1983, p. 976.

* cited by examiner

*Primary Examiner*—Paul P. Gordon

(57) ABSTRACT

A system for dispensing medications in a health care institution includes a computer system connected to control a plurality of remote medication dispensers. Pharmacy terminals are provided for entering medication orders and software in the computer system controls the dispensers to dispene medications according to the orders specified. The system includes support for dispensing medications from floor stocks. In either case, medications are administered in accordance with instructions from the computer system generated in accordance with said orders. The system further includes software for identifying medication duplications and potentially dangerous drug interactions based on orders entered into the system at the pharmacy. Inventory control and restocking features are also provided.

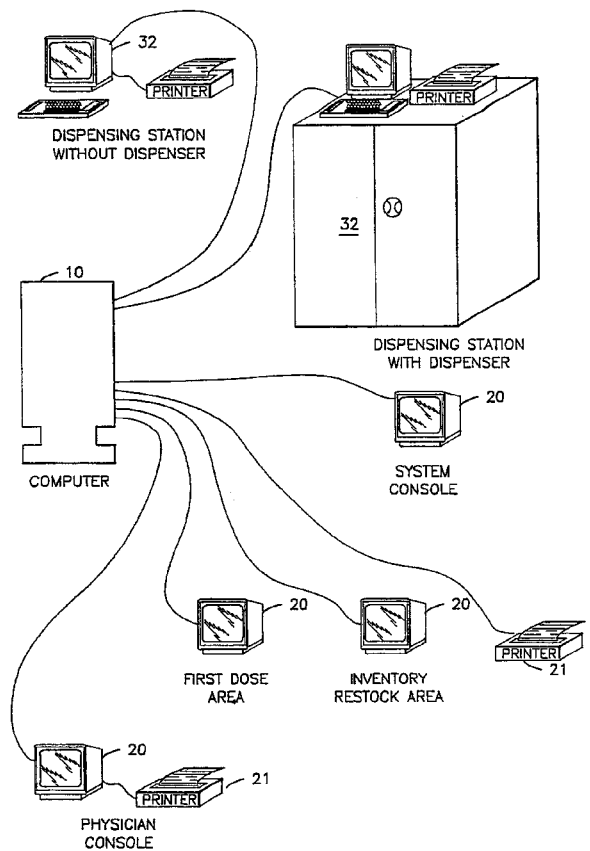

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 1–21 and 68–93 is confirmed.

Claims 22–41, 43–50, 52–67 and 94–97 are cancelled.

Claims 42 and 51 are determined to be patentable as amended.

42. A system for dispensing medications in unit dose packages to patients in a health care institution, comprising:
  one or more dispensing cabinet means for holding a plurality of different types of said medications in unit dose packages, and each selectively controllable for dispensing any one of said different types of medications one or more of said unit dose packages at a time;
  a dispensing cabinet printer means for each of said dispensing cabinet means;
  control means connected for controlling said dispensing cabinet means and said printer means, said control means including:
  (a) database means for holding medication order data specifying medication orders for patients in said institution in accordance with medication prescriptions for said patients, each said order specifying the medication dose, the scheduled times for administration of said medication dose and which of said dispensing cabinet means it is to be dispensed from;
  (b) dispensing control means including a dispensing cabinet input means for each said dispensing cabinet means so that each said dispensing cabinet means has an associated input means, said input means for entering a request to dispense medications for a specified patient from its associated dispensing cabinet means, said control means responsive to a said request for controlling a said dispensing cabinet means to cause it to selectively dispense for said specified patient each said dose ordered to be administered to said specified patient according to said orders, each said dose being dispensed from said cabinet means in said unit dose packages, said dispensing control means capable of causing any one of said unit dose packages of any of said different types of medications to be dispensed for any one of said patients[;] *and for each said dose ordered to be administered as-needed said scheduled times in said data specify a predetermined quantity of dose to be administered no more often than a predetermined number of hours, and further wherein said dispensing control means includes timing means responsive to a said request for preventing said as-needed ordered medication from being dispensed from said dispenser cabinet means at the time of said request if said predetermined quantity of doses have been dispensed within said predetermined number of hours;* and
  (c) report generating means responsive to said data for preparing a medication requirement report for each of said dispensing cabinet means and for causing said medicatio requirement report to be printed on said printer means for each said dispensing cabinet means, said medication requirement report having information on each said dose dispensed for said patients, including the dose and scheduled time for administration, whereby said doses dispensed from said dispensing cabinet means can be taken and administered to said patients in accordance with said medication requirement report.

51. A system according to claim [50] *42* further wherein for said as-needed ordered medications said data specifies a maximum number of doses to be administered during a predetermined block of time and further wherein said timing means includes means for preventing more than said maximum number of doses to be dispensed during said block of time.

* * * * *